United States Patent
Kaplan et al.

(10) Patent No.: US 10,398,502 B2
(45) Date of Patent: Sep. 3, 2019

(54) ENERGY DELIVERY DEVICES AND METHODS

(71) Applicant: Asthmatx, Inc., Sunnyvale, CA (US)

(72) Inventors: Gary S. Kaplan, Mountain View, CA (US); Christopher J. Danek, San Carlos, CA (US); William J. Wizeman, Mountain View, CA (US); Timothy R. Dalbec, Saratoga, CA (US); Noah D. Webster, San Francisco, CA (US); Huy D. Phan, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 476 days.

(21) Appl. No.: 14/861,647

(22) Filed: Sep. 22, 2015

(65) Prior Publication Data

US 2016/0008066 A1  Jan. 14, 2016

Related U.S. Application Data

(63) Continuation of application No. 14/511,298, filed on Oct. 10, 2014, now abandoned, which is a continuation of application No. 13/860,216, filed on Apr. 10, 2013, now abandoned, which is a continuation of application No. 13/087,161, filed on Apr. 14, 2011, now abandoned, which is a
(Continued)

(51) Int. Cl.
| | |
|---|---|
| *A61B 18/14* | (2006.01) |
| *A61F 7/12* | (2006.01) |
| *A61B 18/18* | (2006.01) |
| *A61N 1/05* | (2006.01) |
| *A61B 18/00* | (2006.01) |

(52) U.S. Cl.
CPC .......... *A61B 18/1492* (2013.01); *A61B 18/18* (2013.01); *A61F 7/123* (2013.01); *A61N 1/05* (2013.01); *A61B 2018/00214* (2013.01); *A61B 2018/00267* (2013.01); *A61B 2018/00541* (2013.01); *A61B 2018/00797* (2013.01); *A61B 2018/1437* (2013.01)

(58) Field of Classification Search
CPC combination set(s) only.
See application file for complete search history.

(56) References Cited

U.S. PATENT DOCUMENTS

| 1,155,169 A | 9/1915 | Starkweather |
| 1,207,479 A | 12/1916 | Bisgaard |
| (Continued) | | |

FOREIGN PATENT DOCUMENTS

| EP | 189329 A3 | 6/1987 |
| EP | 908713 A1 | 4/1999 |
| (Continued) | | |

OTHER PUBLICATIONS

Co-pending U.S. Appl. No. 09/095,323, filed Jun. 10, 1998.
(Continued)

*Primary Examiner* — Joseph A Stoklosa
*Assistant Examiner* — Adam J Avigan
(74) *Attorney, Agent, or Firm* — Bookoff McAndrews, PLLC

(57) ABSTRACT

This relates to methods and devices for achieving contact between the wall of a cavity or passageway and a medical device when used in tortuous anatomy.

6 Claims, 21 Drawing Sheets

Related U.S. Application Data continuation of application No. 11/618,533, filed on Dec. 29, 2006, now Pat. No. 7,949,407.

(56) References Cited

U.S. PATENT DOCUMENTS

| | | |
|---|---|---|
| 2,072,346 A | 3/1937 | Smith |
| 3,320,957 A | 5/1967 | Edward |
| 3,568,659 A | 3/1971 | Karnegis |
| 3,667,476 A | 6/1972 | Muller |
| 3,692,029 A | 9/1972 | Adair |
| 4,461,283 A | 7/1984 | Doi |
| 4,503,855 A | 3/1985 | Maslanka |
| 4,522,212 A | 6/1985 | Gelinas et al. |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,643,186 A | 2/1987 | Rosen et al. |
| 4,674,497 A | 6/1987 | Ogasawara |
| 4,706,688 A | 11/1987 | Don Michael et al. |
| 4,709,698 A | 12/1987 | Johnston et al. |
| 4,799,479 A | 1/1989 | Spears |
| 4,802,492 A | 2/1989 | Grunstein |
| 4,825,871 A | 5/1989 | Cansell |
| 4,827,935 A | 5/1989 | Geddes et al. |
| 4,862,886 A | 9/1989 | Clarke et al. |
| 4,920,978 A | 5/1990 | Colvin |
| 4,955,377 A | 9/1990 | Lennox et al. |
| 4,967,765 A | 11/1990 | Turner et al. |
| 4,976,709 A | 12/1990 | Sand |
| 5,010,892 A | 4/1991 | Colvin et al. |
| 5,019,075 A | 5/1991 | Spears et al. |
| 5,053,033 A | 10/1991 | Clarke |
| 5,056,519 A | 10/1991 | Vince |
| 5,061,274 A | 10/1991 | Kensey |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,106,360 A | 4/1992 | Ishiwara et al. |
| 5,109,830 A | 5/1992 | Cho |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,170,803 A | 12/1992 | Hewson et al. |
| 5,174,288 A | 12/1992 | Bardy et al. |
| 5,188,602 A | 2/1993 | Nichols |
| 5,191,883 A | 3/1993 | Lennox et al. |
| 5,215,103 A | 6/1993 | Desai |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,292,331 A | 3/1994 | Boneau |
| 5,293,869 A | 3/1994 | Edwards et al. |
| 5,309,910 A | 5/1994 | Edwards et al. |
| 5,311,866 A | 5/1994 | Kagan et al. |
| 5,313,943 A | 5/1994 | Houser et al. |
| 5,324,284 A | 6/1994 | Imran |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,368,592 A | 11/1994 | Stern et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,394,880 A | 3/1995 | Atlee, III |
| 5,396,887 A | 3/1995 | Imran |
| 5,400,783 A | 3/1995 | Pomeranz et al. |
| 5,409,469 A | 4/1995 | Schaerf |
| 5,411,025 A | 5/1995 | Webster |
| 5,415,166 A | 5/1995 | Imran |
| 5,415,656 A | 5/1995 | Tihon et al. |
| 5,417,687 A | 5/1995 | Nardella et al. |
| 5,423,744 A | 6/1995 | Gencheff et al. |
| 5,423,811 A | 6/1995 | Imran et al. |
| 5,425,703 A | 6/1995 | Feiring |
| 5,431,696 A | 7/1995 | Atlee, III |
| 5,433,730 A | 7/1995 | Alt |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,464,404 A | 11/1995 | Abela et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,500,011 A | 3/1996 | Desai |
| 5,505,728 A | 4/1996 | Ellman et al. |
| 5,505,730 A | 4/1996 | Edwards |
| 5,509,411 A | 4/1996 | Littmann et al. |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,558,073 A | 9/1996 | Pomeranz et al. |
| 5,562,608 A | 10/1996 | Sekins et al. |
| 5,562,619 A | 10/1996 | Mirarchi et al. |
| 5,571,088 A | 11/1996 | Lennox et al. |
| 5,578,067 A | 11/1996 | Ekwall et al. |
| 5,582,609 A | 12/1996 | Swanson et al. |
| 5,588,432 A | 12/1996 | Crowley |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,623,940 A | 4/1997 | Daikuzono |
| 5,624,439 A | 4/1997 | Edwards et al. |
| 5,626,618 A | 5/1997 | Ward et al. |
| 5,628,313 A | 5/1997 | Webster |
| 5,630,425 A | 5/1997 | Panescu et al. |
| 5,630,794 A | 5/1997 | Lax et al. |
| 5,634,471 A | 6/1997 | Fairfax et al. |
| 5,647,870 A | 7/1997 | Kordis et al. |
| 5,678,535 A | 10/1997 | Dimarco |
| 5,680,860 A | 10/1997 | Imran |
| 5,681,280 A | 10/1997 | Rusk et al. |
| 5,681,308 A | 10/1997 | Edwards et al. |
| 5,693,078 A | 12/1997 | Desai et al. |
| 5,699,799 A | 12/1997 | Xu et al. |
| 5,707,352 A | 1/1998 | Sekins et al. |
| 5,720,775 A | 2/1998 | Larnard |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,728,094 A | 3/1998 | Edwards |
| 5,730,128 A | 3/1998 | Pomeranz et al. |
| 5,730,726 A | 3/1998 | Klingenstein |
| 5,730,741 A | 3/1998 | Horzewski et al. |
| 5,740,808 A | 4/1998 | Panescu et al. |
| 5,752,518 A | 5/1998 | McGee et al. |

(56) References Cited

U.S. PATENT DOCUMENTS

| | | |
|---|---|---|
| 5,755,753 A | 5/1998 | Knowlton |
| 5,759,158 A | 6/1998 | Swanson |
| 5,769,846 A | 6/1998 | Edwards et al. |
| 5,772,590 A | 6/1998 | Webster |
| 5,775,338 A | 7/1998 | Hastings |
| 5,779,669 A | 7/1998 | Haissaguerre et al. |
| 5,779,698 A | 7/1998 | Clayman et al. |
| 5,782,239 A | 7/1998 | Webster |
| 5,782,795 A | 7/1998 | Bays |
| 5,782,827 A | 7/1998 | Gough et al. |
| 5,782,899 A | 7/1998 | Imran |
| 5,792,064 A | 8/1998 | Panescu et al. |
| 5,795,303 A | 8/1998 | Swanson et al. |
| 5,807,306 A | 9/1998 | Shapland et al. |
| 5,810,807 A | 9/1998 | Ganz et al. |
| 5,814,029 A | 9/1998 | Hassett |
| 5,823,189 A | 10/1998 | Kordis |
| 5,824,359 A | 10/1998 | Khan et al. |
| 5,827,277 A | 10/1998 | Edwards |
| 5,833,632 A | 11/1998 | Jacobsen et al. |
| 5,836,946 A | 11/1998 | Diaz et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,846,238 A | 12/1998 | Jackson et al. |
| 5,848,969 A | 12/1998 | Panescu et al. |
| 5,848,972 A | 12/1998 | Triedman et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,685 A | 2/1999 | Powell et al. |
| 5,868,740 A | 2/1999 | Leveen et al. |
| 5,871,443 A | 2/1999 | Edwards et al. |
| 5,871,523 A | 2/1999 | Fleischman et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,135 A | 4/1999 | Jackson et al. |
| 5,891,136 A | 4/1999 | McGee et al. |
| 5,891,138 A | 4/1999 | Tu et al. |
| 5,893,847 A | 4/1999 | Kordis |
| 5,897,554 A | 4/1999 | Chia et al. |
| 5,899,882 A | 5/1999 | Waksman et al. |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,911,218 A | 6/1999 | Dimarco |
| 5,916,235 A | 6/1999 | Guglielmi |
| 5,919,147 A | 7/1999 | Jain |
| 5,921,999 A | 7/1999 | Dileo |
| 5,928,228 A | 7/1999 | Kordis et al. |
| 5,935,079 A | 8/1999 | Swanson et al. |
| 5,941,869 A | 8/1999 | Patterson et al. |
| 5,944,713 A | 8/1999 | Schuman |
| 5,951,494 A | 9/1999 | Wang et al. |
| 5,954,661 A | 9/1999 | Greenspon et al. |
| 5,954,662 A | 9/1999 | Swanson et al. |
| 5,954,717 A | 9/1999 | Behl et al. |
| 5,957,842 A | 9/1999 | Littmann et al. |
| 5,957,961 A | 9/1999 | Maguire et al. |
| 5,964,753 A | 10/1999 | Edwards |
| 5,964,796 A | 10/1999 | Imran |
| 5,968,087 A | 10/1999 | Hess et al. |
| 5,971,983 A | 10/1999 | Lesh |
| 5,972,026 A | 10/1999 | Laufer et al. |
| 5,979,456 A | 11/1999 | Magovern |
| 5,980,563 A | 11/1999 | Tu et al. |
| 5,991,650 A | 11/1999 | Swanson et al. |
| 5,992,419 A | 11/1999 | Sterzer et al. |
| 5,993,462 A | 11/1999 | Pomeranz et al. |
| 5,997,534 A | 12/1999 | Tu et al. |
| 5,999,855 A | 12/1999 | Dimarco |
| 6,003,517 A | 12/1999 | Sheffield et al. |
| 6,004,269 A | 12/1999 | Crowley et al. |
| 6,006,755 A | 12/1999 | Edwards |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. |
| 6,023,638 A | 2/2000 | Swanson |
| 6,024,740 A | 2/2000 | Lesh et al. |
| 6,029,091 A | 2/2000 | De La Rama et al. |
| 6,033,397 A | 3/2000 | Laufer et al. |
| 6,036,687 A | 3/2000 | Laufer et al. |
| 6,036,689 A | 3/2000 | Tu et al. |
| 6,039,731 A | 3/2000 | Taylor et al. |
| 6,045,549 A | 4/2000 | Smethers et al. |
| 6,045,550 A | 4/2000 | Simpson et al. |
| 6,050,992 A | 4/2000 | Nichols |
| 6,053,172 A | 4/2000 | Hovda et al. |
| 6,056,744 A | 5/2000 | Edwards |
| 6,056,769 A | 5/2000 | Epstein et al. |
| 6,066,132 A | 5/2000 | Chen et al. |
| 6,071,279 A | 6/2000 | Whayne et al. |
| 6,071,280 A | 6/2000 | Edwards et al. |
| 6,071,281 A | 6/2000 | Burnside et al. |
| 6,071,282 A | 6/2000 | Fleischman |
| 6,083,255 A | 7/2000 | Laufer et al. |
| 6,092,528 A | 7/2000 | Edwards |
| 6,102,886 A | 8/2000 | Lundquist et al. |
| 6,119,030 A | 9/2000 | Morency |
| 6,123,703 A | 9/2000 | Tu et al. |
| 6,123,718 A | 9/2000 | Tu et al. |
| H1905 H | 10/2000 | Hill |
| 6,129,751 A | 10/2000 | Lucchesi et al. |
| 6,139,527 A | 10/2000 | Laufer et al. |
| 6,142,993 A | 11/2000 | Whayne et al. |
| 6,143,013 A | 11/2000 | Samson et al. |
| 6,149,647 A | 11/2000 | Tu et al. |
| 6,152,899 A | 11/2000 | Farley et al. |
| 6,159,194 A | 12/2000 | Eggers et al. |
| 6,164,283 A | 12/2000 | Lesh |
| 6,179,833 B1 | 1/2001 | Taylor |
| 6,183,468 B1 | 2/2001 | Swanson et al. |
| 6,198,970 B1 | 3/2001 | Freed et al. |
| 6,200,311 B1 | 3/2001 | Danek et al. |
| 6,200,332 B1 | 3/2001 | Del Giglio |
| 6,200,333 B1 | 3/2001 | Laufer |
| 6,210,367 B1 | 4/2001 | Carr |
| 6,214,002 B1 | 4/2001 | Fleischman et al. |
| 6,216,043 B1 | 4/2001 | Swanson et al. |
| 6,216,044 B1 | 4/2001 | Kordis |
| 6,216,704 B1 * | 4/2001 | Ingle ............... A61B 18/1482 128/898 |
| 6,217,576 B1 | 4/2001 | Tu et al. |
| 6,235,024 B1 | 5/2001 | Tu |
| 6,241,727 B1 | 6/2001 | Tu et al. |
| 6,251,104 B1 | 6/2001 | Kesten et al. |
| 6,254,598 B1 | 7/2001 | Edwards et al. |
| 6,258,083 B1 | 7/2001 | Daniel et al. |
| 6,258,087 B1 | 7/2001 | Edwards et al. |
| 6,270,476 B1 | 8/2001 | Santoianni et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,290 B1 | 9/2001 | Perkins et al. |
| 6,296,639 B1 | 10/2001 | Truckai et al. |
| 6,299,633 B1 | 10/2001 | Laufer |
| 6,322,559 B1 | 11/2001 | Daulton et al. |
| 6,322,584 B2 | 11/2001 | Ingle et al. |
| 6,338,727 B1 | 1/2002 | Noda et al. |
| 6,338,836 B1 | 1/2002 | Kuth et al. |
| 6,379,352 B1 | 4/2002 | Reynolds et al. |
| 6,409,723 B1 | 6/2002 | Edwards |
| 6,411,852 B1 | 6/2002 | Danek et al. |
| 6,416,511 B1 | 7/2002 | Lesh et al. |
| 6,423,105 B1 | 7/2002 | Iijima et al. |
| 6,425,895 B1 | 7/2002 | Swanson et al. |

(56) References Cited

U.S. PATENT DOCUMENTS

| | | |
|---|---|---|
| 6,440,129 B1 | 8/2002 | Simpson |
| 6,442,435 B2 | 8/2002 | King et al. |
| 6,460,545 B2 | 10/2002 | Kordis |
| 6,463,331 B1 | 10/2002 | Edwards |
| 6,488,673 B1 | 12/2002 | Laufer et al. |
| 6,493,589 B1 | 12/2002 | Medhkour et al. |
| 6,496,738 B2 | 12/2002 | Carr |
| 6,514,246 B1 | 2/2003 | Swanson et al. |
| 6,526,320 B2 | 2/2003 | Mitchell |
| 6,529,756 B1 | 3/2003 | Phan et al. |
| 6,539,265 B2 | 3/2003 | Medhkour et al. |
| 6,544,226 B1 | 4/2003 | Gaiser et al. |
| 6,544,262 B2 | 4/2003 | Fleischman |
| 6,547,788 B1 | 4/2003 | Maguire et al. |
| 6,572,612 B2 | 6/2003 | Stewart et al. |
| 6,575,623 B2 | 6/2003 | Werneth |
| 6,582,427 B1 | 6/2003 | Goble et al. |
| 6,582,430 B2 | 6/2003 | Hall |
| 6,589,235 B2 | 7/2003 | Wong et al. |
| 6,610,054 B1 | 8/2003 | Edwards et al. |
| 6,620,159 B2 | 9/2003 | Hegde |
| 6,626,903 B2 | 9/2003 | McGuckin et al. |
| 6,629,951 B2 | 10/2003 | Laufer et al. |
| 6,634,363 B1 | 10/2003 | Danek et al. |
| 6,638,273 B1 | 10/2003 | Farley et al. |
| 6,640,120 B1 | 10/2003 | Swanson et al. |
| 6,645,199 B1 | 11/2003 | Jenkins et al. |
| 6,645,200 B1 | 11/2003 | Koblish et al. |
| 6,645,205 B2 | 11/2003 | Ginn |
| 6,652,548 B2 | 11/2003 | Evans et al. |
| 6,669,693 B2 | 12/2003 | Friedman |
| 6,673,068 B1 | 1/2004 | Berube |
| 6,685,702 B2 | 2/2004 | Quijano et al. |
| 6,692,492 B2 | 2/2004 | Simpson et al. |
| 6,692,494 B1 | 2/2004 | Cooper et al. |
| 6,699,243 B2 | 3/2004 | West et al. |
| 6,712,812 B2 | 3/2004 | Roschak et al. |
| 6,714,822 B2 | 3/2004 | King et al. |
| 6,723,091 B2 | 4/2004 | Goble et al. |
| 6,740,082 B2 | 5/2004 | Shadduck |
| 6,743,197 B1 | 6/2004 | Edwards |
| 6,749,604 B1 | 6/2004 | Eggers et al. |
| 6,749,606 B2 | 6/2004 | Keast et al. |
| 6,749,607 B2 | 6/2004 | Edwards et al. |
| 6,755,849 B1 * | 6/2004 | Gowda ............ A61B 18/18 606/13 |
| 6,767,347 B2 | 7/2004 | Sharkey et al. |
| 6,770,070 B1 | 8/2004 | Balbierz |
| 6,802,843 B2 | 10/2004 | Truckai et al. |
| 6,805,131 B2 | 10/2004 | Kordis |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,866,662 B2 | 3/2005 | Fuimaono et al. |
| 6,869,437 B1 | 3/2005 | Hausen et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,954,977 B2 | 10/2005 | Maguire et al. |
| 6,976,991 B2 | 12/2005 | Hebert et al. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,118,568 B2 | 10/2006 | Hassett et al. |
| 7,122,033 B2 | 10/2006 | Wood |
| 7,186,251 B2 | 3/2007 | Malecki et al. |
| 7,198,635 B2 | 4/2007 | Danek et al. |
| 7,200,445 B1 | 4/2007 | Dalbec et al. |
| 7,264,002 B2 | 9/2007 | Danek et al. |
| 7,273,055 B2 | 9/2007 | Danek et al. |
| 7,371,231 B2 | 5/2008 | Rioux et al. |
| 7,387,126 B2 | 6/2008 | Cox et al. |
| 7,425,212 B1 | 9/2008 | Danek et al. |
| 7,556,624 B2 | 7/2009 | Laufer et al. |
| 7,628,789 B2 | 12/2009 | Soltesz et al. |
| 7,949,407 B2 | 5/2011 | Kaplan et al. |
| 8,568,403 B2 | 10/2013 | Soltesz et al. |
| 2002/0072737 A1 | 6/2002 | Belden et al. |
| 2002/0147391 A1 | 10/2002 | Morency |
| 2002/0173785 A1 | 11/2002 | Spear et al. |
| 2002/0198523 A1 | 12/2002 | Behl |
| 2003/0050631 A1 | 3/2003 | Mody et al. |
| 2003/0051733 A1 | 3/2003 | Kotmel et al. |
| 2003/0065371 A1 | 4/2003 | Satake |
| 2003/0233099 A1 * | 12/2003 | Danaek ............ A61N 1/403 606/96 |
| 2004/0047855 A1 | 3/2004 | Ingenito |
| 2004/0102804 A1 | 5/2004 | Chin |
| 2004/0153056 A1 | 8/2004 | Muller et al. |
| 2004/0249401 A1 | 12/2004 | Rabiner et al. |
| 2005/0010270 A1 | 1/2005 | Laufer |
| 2005/0096644 A1 | 5/2005 | Hall et al. |
| 2005/0096647 A1 * | 5/2005 | Steinke ............ A61B 18/1492 606/41 |
| 2005/0154386 A1 | 7/2005 | West et al. |
| 2005/0182393 A1 | 8/2005 | Abboud et al. |
| 2005/0182431 A1 | 8/2005 | Hausen et al. |
| 2005/0203503 A1 | 9/2005 | Edwards et al. |
| 2005/0240176 A1 | 10/2005 | Oral et al. |
| 2006/0062808 A1 | 3/2006 | Laufer et al. |
| 2006/0089637 A1 | 4/2006 | Werneth et al. |
| 2006/0135953 A1 | 6/2006 | Kania et al. |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0264772 A1 | 11/2006 | Aljuri et al. |
| 2007/0100390 A1 | 5/2007 | Danaek et al. |
| 2007/0106296 A1 | 5/2007 | Laufer et al. |
| 2007/0118184 A1 | 5/2007 | Danek et al. |
| 2007/0123958 A1 | 5/2007 | Laufer |
| 2007/0123961 A1 | 5/2007 | Danek et al. |
| 2008/0097424 A1 | 4/2008 | Wizeman et al. |
| 2008/0255642 A1 | 10/2008 | Zarins et al. |
| 2009/0018538 A1 | 1/2009 | Webster et al. |
| 2009/0043301 A1 | 2/2009 | Jarrard et al. |
| 2009/0069797 A1 | 3/2009 | Danek et al. |
| 2009/0306644 A1 | 12/2009 | Mayse et al. |
| 2010/0160906 A1 | 6/2010 | Jarrard |

FOREIGN PATENT DOCUMENTS

| | | |
|---|---|---|
| EP | 908150 B1 | 5/2003 |
| EP | 1297795 B1 | 8/2005 |
| FR | 2659240 B1 | 7/1997 |
| JP | 7289557 A | 11/1995 |
| RU | 2053814 C1 | 2/1996 |
| RU | 2091054 C1 | 9/1997 |
| WO | WO-1989011311 A1 | 11/1989 |
| WO | WO-1993004734 A1 | 3/1993 |
| WO | WO-1995002370 A2 | 1/1995 |
| WO | WO-9502370 A3 | 3/1995 |
| WO | WO-1995010322 A1 | 4/1995 |
| WO | WO-1996004860 A1 | 2/1996 |
| WO | WO-1996010961 A1 | 4/1996 |
| WO | WO-1997032532 A1 | 9/1997 |
| WO | WO-1997033715 A1 | 9/1997 |
| WO | WO-1997037715 A1 | 10/1997 |
| WO | WO-1998044854 A1 | 10/1998 |
| WO | WO-1998052480 A1 | 11/1998 |
| WO | WO-9858681 A2 | 12/1998 |
| WO | WO-1998056324 A1 | 12/1998 |
| WO | WO-1999003413 A1 | 1/1999 |
| WO | WO-1998058681 A3 | 3/1999 |
| WO | WO-1999013779 A2 | 3/1999 |
| WO | WO-1999034741 A1 | 7/1999 |
| WO | WO-1999044506 A1 | 9/1999 |
| WO | WO-1999045855 A1 | 9/1999 |
| WO | WO-2000051510 A1 | 9/2000 |

(56) References Cited

FOREIGN PATENT DOCUMENTS

| WO | WO-2001003642 A1 | 1/2001 |
|---|---|---|
| WO | WO-0232334 A1 | 4/2002 |
| WO | WO-2006052940 A2 | 5/2006 |

OTHER PUBLICATIONS

Dierkesmann R., "Indication and Results of Endobronchial Laser Therapy," Lung, 1990, vol. 168, pp. 1095-1102.

Hogg J. C., "The Pathology of Asthma," APMIS, 1997, vol. 105 (10), pp. 735-745.

Ivanyuta O.M., et al., "Effect of Low-Power Laser Irradiation of Bronchial Mucosa on the State of Systemic and Local Immunity in Patients with Chronic Bronchitis," Problemy Tuberkuleza, 1991, vol. 6, pp. 26-29.

Johnson S. R., et al., "Synthetic Functions of Airway Smooth Muscle in Asthma," Trends Pharmacological Sciences, 1997, vol. 18 (8), pp. 288-292.

Macklem P. T., "Mechanical Factors Determining Maximum Bronchoconstriction," European Respiratory Journal, 1989, vol. 6. pp. 516s-519s.

Netter F.H., "Respiratory System: A Compilation of Paintings Depicting Anatomy and Embryology, Physiology, Pathology, Pathophysiology, and Clinical Features and Treatment of Diseases,In the CIBA Collection of Medical Illustrations M.B. Divertie, ed., Summit: New Jerse," 1979, vol. 7, pp. 119-135.

Notice of Opposition to European Patent No. EP2320821B1, Jul. 23, 2013, 24 pages.

PCT International search report for application No. PCT/US05/40378 dated Aug. 8, 2006, 2 pages.

PCT International search report for application No. PCT/US05/41244 dated Mar. 20, 2007, 1 page.

Provotorov V.M., et al., "The Clinical Efficacy of Treating Patients with Nonspecific Lung Diseases Using Low-energy Laser Irradiation and Intrapulmonary Drug Administration," Terapevticheskii Arkhiv, 1991, vol. 62 (12), pp. 18-23.

Reply of Patent Proprietor to Notice of Opposition to European Patent No. EP 2320821B1, Mar. 10, 2014, 26 pages.

Summons to Attend Oral Proceedings Pursuant to Rule 115(1) EPC in Opposition to European Patent No. EP2320821B1, Jul. 14, 2014, 5 pages.

Vorotnev A.I., et al., "The Treatment of Patients with Chronic Obstructive Bronchitis by Using a Low-power Laser at a General Rehabilitation Center," Terapevticheskii Arkhiv, 1997, vol. 69 (3), pp. 17-19.

Wiggs B.R., et al., "On the Mechanism of Mucosal Folding in Normal and Asthmatic Airways," Journal of Applied Physiology, 1997, vol. 83 (6), pp. 1814-1821.

* cited by examiner

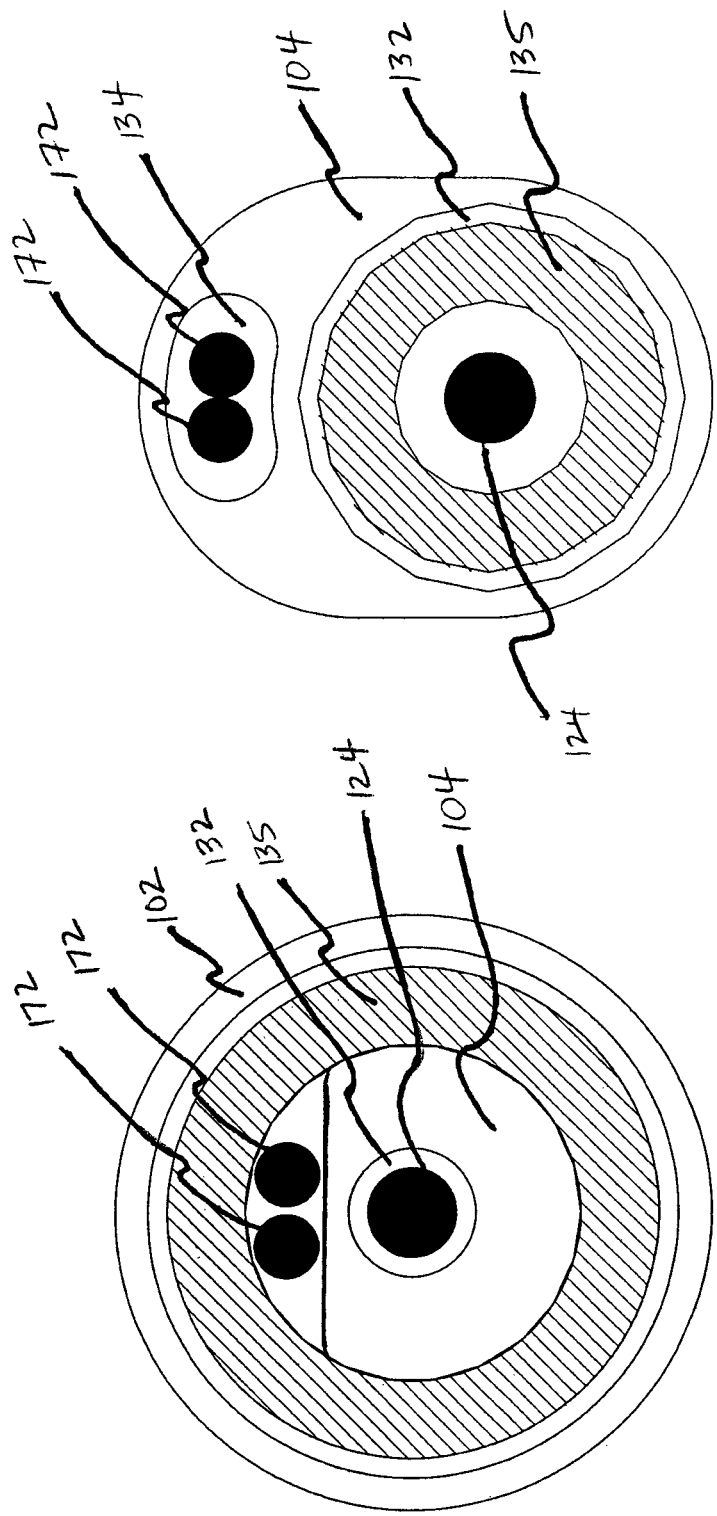

FIG. 4A      FIG. 4B

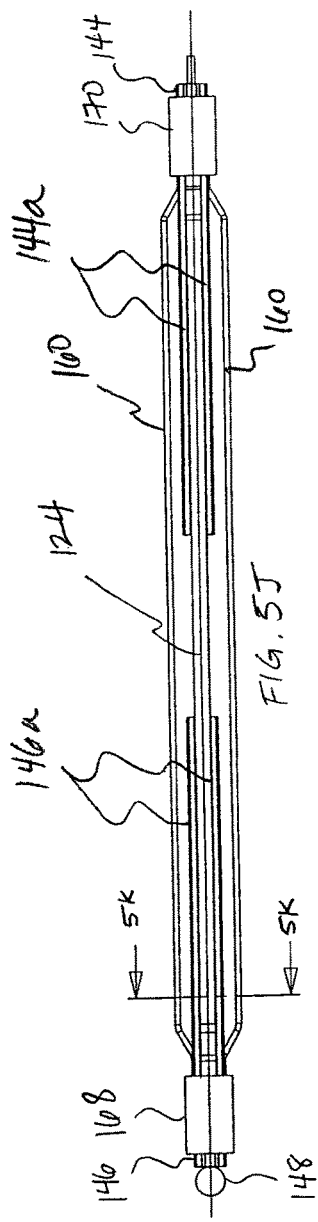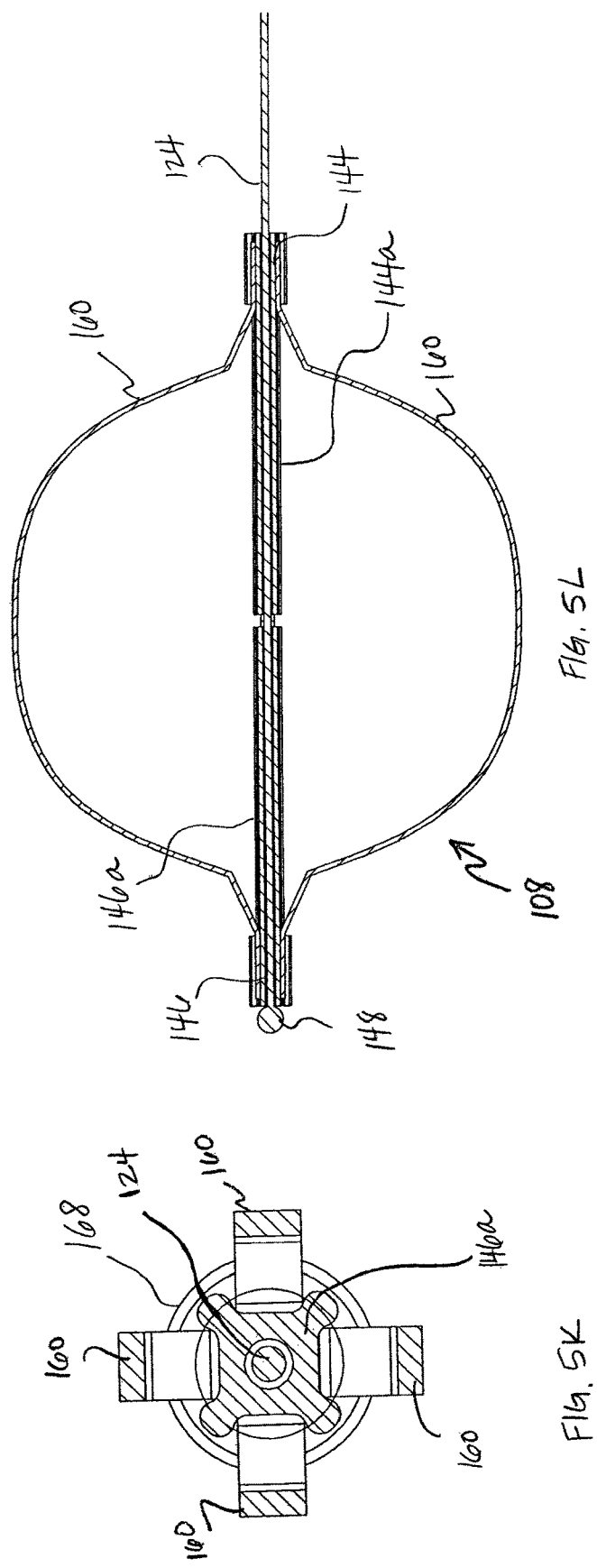

ENERGY DELIVERY DEVICES AND METHODS

CROSS REFERENCE TO RELATED APPLICATIONS

This application is a continuation of U.S. patent application Ser. No. 14/511,298, filed on Oct. 10, 2014, now abandoned, which is a continuation of U.S. patent application Ser. No. 13/860,216, filed on Apr. 10, 2013, now abandoned, which is a continuation of U.S. patent application Ser. No. 13/087,161, filed on Apr. 14, 2011, now abandoned, which is a continuation of U.S. patent application Ser. No. 11/618,533, filed on Dec. 29, 2006, now U.S. Pat. No. 7,949,407, the entireties of each of which are incorporated herein by reference. This application is related to U.S. patent application Ser. No. 11/256,295, filed on Oct. 21, 2005, now U.S. Pat. No. 7,200,445, U.S. patent application Ser. No. 11/420,442, filed on May 25, 2006, now U.S. Pat. No. 7,853,331, International Application No. PCT/US2005/040378, filed on Nov. 7, 2005, U.S. Provisional Patent Application No. 60/625,256, filed on Nov. 5, 2004, and U.S. Provisional Patent Application No. 60/650,368, filed on Feb. 4, 2005, the entireties of each of which are incorporated herein by reference.

BACKGROUND OF THE INVENTION

Asthma is a disease in which (i) bronchoconstriction, (ii) excessive mucus production, and (iii) inflammation and swelling of airways occur, causing widespread but variable airflow obstruction thereby making it difficult for the asthma sufferer to breathe. Asthma is a chronic disorder, primarily characterized by persistent airway inflammation. However, asthma is further characterized by acute episodes of additional airway narrowing via contraction of hyper-responsive airway smooth muscle.

Asthma is managed pharmacologically by: (1) long term control through use of anti-inflammatories and long-acting bronchodilators and (2) short term management of acute exacerbations through use of short-acting bronchodilators. Both of these approaches require repeated and regular use of the prescribed drugs. High doses of corticosteroid anti-inflammatory drugs can have serious side effects that require careful management. In addition, some patients are resistant to steroid treatment. The difficulty involved in patient compliance with pharmacologic management and the difficulty of avoiding stimulus that triggers asthma are common barriers to successful asthma management.

Current management techniques are neither completely successful nor free from side effects. Presently, a new treatment for asthma is showing promise. This treatment comprises the application of energy to the airway smooth muscle tissue. Additional information about this treatment may be found in commonly assigned patents and applications in U.S. Pat. Nos. 6,411,852, 6,634,363 and U.S. published application nos. US-2005-0010270-A1 and US-2002-0091379-A1, the entirety of each of which is incorporated by reference.

The application of energy to airway smooth muscle tissue, when performed via insertion of a treatment device into the bronchial passageways, requires navigation through tortuous anatomy as well as the ability to treat a variety of sizes of bronchial passageways. As discussed in the above referenced patents and applications, use of an RF energy delivery device is one means of treating smooth muscle tissue within the bronchial passageways.

FIG. 1A illustrates a bronchial tree 90. As noted herein, devices treating areas of the lungs must have a construction that enables navigation through the tortuous passages. As shown, the various bronchioles 92 decrease in size and have many branches 96 as they extend into the right and left bronchi 94. Accordingly, an efficient treatment requires devices that are able to treat airways of varying sizes as well as function properly when repeatedly deployed after navigating through the tortuous anatomy.

Tortuous anatomy also poses challenges when the treatment device requires mechanical actuation of the treatment portion (e.g., expansion of a treatment element at a remote site). In particular, attempting to actuate a member may be difficult in view of the fact that the force applied at the operator's hand-piece must translate to the distal end of the device. The strain on the operator is further intensified given that the operator must actuate the distal end of the device many times to treat various portions of the anatomy. When a typical device is contorted after being advanced to a remote site in the lungs, the resistance within the device may be amplified given that internal components are forced together.

It is also noted that the friction of polymers is different from that of metals. Most polymers are viscoelastic and deform to a greater degree under load than metals. Accordingly, when energy or force is applied to move two polymers against each other, a significant part of friction between the polymers is the energy loss through inelastic hysteresis. In addition, adhesion between polymers also plays a significant part in the friction between such polymers.

In addition to basic considerations of navigation and site access, there exists the matter of device orientation and tissue contact at the treatment site. Many treatment devices make contact or are placed in close proximity to the target tissue. Yet, variances in the construction of the treatment device may hinder proper alignment or orientation of the device. For example, in the case of a device having a basket-type energy transfer element that is deployed intralumenally, the treatment may benefit from uniform contact of basket elements around the perimeter of the lumen. However, in this case, design or manufacturing variances may tend to produce a device where the angle between basket elements is not uniform. This problem tends to be exacerbated after repeated actuation of the device and/or navigating the device through tortuous anatomy when the imperfections of the device become worsened through plastic deformation of the individual components. Experience demonstrates that once a member becomes predisposed to splaying (i.e., not maintaining the desired angular separation from an adjacent element), or inverting (i.e., buckling inward instead of deploying outward), the problem is unlikely to resolve itself without requiring attention by the operator. As a result, the operator is forced to remove the device from the patient, make adjustments, then restart treatment. This interruption tends to increase the time of the treatment session.

As one example, commonly assigned U.S. Pat. No. 6,411,852, incorporated by reference herein, describes a treatment for asthma using devices having flexible electrode members that can be expanded to better fill a space (e.g., the lumen of an airway.) However, the tortuous nature of the airways was found to cause significant bending and/or flexure of the distal end of the device. As a result, the spacing of electrode members tended not to be even. In some extreme cases, electrode elements could tend to invert, where instead of expanding an electrode leg would invert behind an opposing leg.

For many treatment devices, the distortion of the energy transfer elements might cause variability in the treatment effect. For example, many RF devices heat tissue based on the tissue's resistive properties. Increasing or decreasing the surface contact between the electrode and tissue often increases or decreases the amount of current flowing through the tissue at the point of contact. This directly affects the extent to which the tissue is heated. Similar concerns may also arise with resistive heating elements, devices used to cool the airway wall by removing heat, or any energy transfer device. In any number of cases, variability of the energy transfer/tissue interface causes variability in treatment results. The consequential risks range from an ineffective treatment to the possibility of patient injury.

Furthermore, most medical practitioners recognize the importance of establishing acceptable contact between the transfer element and tissue. Therefore, distortion of the transfer element or elements increases the procedure time when the practitioner spends an inordinate amount of time adjusting a device to compensate for or avoid such distortion. Such action becomes increasingly problematic in those cases where proper patient management limits the time available for the procedure.

For example, if a patient requires an increasing amount of medication (e.g., sedatives or anesthesia) to remain under continued control for performance of the procedure, then a medical practitioner may limit the procedure time rather than risk overmedicating the patient. As a result, rather than treating the patient continuously to complete the procedure, the practitioner may plan to break the procedure in two or more sessions. Subsequently, increasing the number of sessions poses additional consequences on the part of the patient in cost, the residual effects of any medication, adverse effects of the non-therapeutic portion of the procedure, etc.

In view of the above, the present methods and devices described herein provide an improved means for treating tortuous anatomy such as the bronchial passages. It is noted that the improvements of the present device may be beneficial for use in other parts of the anatomy as well as the lungs.

SUMMARY OF THE INVENTION

The present invention includes devices configured to treat the airways or other anatomical structures, and may be especially useful in tortuous anatomy. The devices described herein are configured to treat with uniform or predictable contact (or near contact) between an active element and tissue. Typically, the invention allows this result with little or no effort by a physician. Accordingly, aspects of the invention offer increased effectiveness and efficiency in carrying out a medical procedure. The increases in effectiveness and efficiency may be especially apparent in using devices having relatively longer active end members.

In view of the above, a variation of the invention includes a catheter for use with a power supply, the catheter comprising a flexible elongate shaft coupled to at least one energy transfer element that is adapted to apply energy to the body lumen. The shaft will have a flexibility to accommodate navigation through tortuous anatomy. The energy transfer elements are described below and include basket type design, or other expandable designs that permit reduction in size or profile to aid in advancing the device to a particular treatment site and then may be expanded to properly treat the target site. The basket type designs may be combined with expandable balloon or other similar structures.

Variations of the device can include an elongate sheath having a near end, a far end adapted for insertion into the body, and having a flexibility to accommodate navigation through tortuous anatomy, the sheath having a passageway extending therethrough, the passageway having a lubricious layer extending from at least a portion of the near end to the far end of the sheath. Where the shaft is slidably located within the passageway of the sheath.

Variations of devices described herein can include a connector for coupling the energy transfer element to the power supply. The connector may be any type of connector commonly used in such applications. Furthermore, the connector may include a cable that is hard-wired to the catheter and connects to a remote power supply. Alternatively, the connector may be an interface that connects to a cable from the power supply.

As noted below, variations of the device allow for reduce friction between the shaft and sheath to allow relatively low force advancement of a distal end of the shaft out of the far end of the sheath for advancement the energy transfer element.

Additional variations of the invention include devices allowing for repeatable deployment of the expandable energy transfer element while maintaining the orientation and/or profile of the components of the energy transfer element. One such example includes an energy transfer basket comprising a plurality of legs, each leg having a distal end and a proximal end, each leg having a flexure length that is less than a full length of the leg. The legs are coupled to near and far alignment components. The near alignment component includes a plurality of near seats extending along an axis of the alignment component. The near alignment component can be secured to the elongate shaft of the device. The far alignment component may have a plurality of far seats extending along an axis of the alignment component, where the plurality of near seats are in alignment with the plurality of far seats. In these variations of the device, each distal end of each leg is nested within a far seat of the far alignment component and each proximal end of each leg is nested within a near seat of the near alignment component such that an angle between adjacent legs is determined by an angle between adjacent near seats and the flexure length of each length is determined by the distance between near and far alignment components.

One or both of the components may include stops that control flexure length of each leg. Such a design increases the likelihood that the flexure of each leg is uniform.

An additional variation of the device includes a catheter for use in tortuous anatomy to deliver energy from a power supply to a body passageway. Such a catheter includes an expandable energy transfer element having a reduced profile for advancement and an expanded profile to contact a surface of the body passageway and an elongate shaft having a near end, a far end adapted for insertion into the body, the expandable energy transfer element coupled to the far end of the shaft, the shaft having a length sufficient to access remote areas in the anatomy. The design of this shaft includes a column strength sufficient to advance the expandable energy transfer element within the anatomy, and a flexibility that permits self-centering of the energy transfer element when expanded to contact the surface of the body passageway.

BRIEF DESCRIPTION OF THE DRAWINGS

Each of the following figures diagrammatically illustrates aspects of the invention. Variation of the invention from the aspects shown in the figures is contemplated.

FIG. 3H illustrates a sheathless device having an oblong or oval shaft cross section.

FIG. 3I illustrates another variation of the device having a D-shaped cross section.

FIGS. 4A-4C illustrate various alignment components of the device.

FIGS. 5J-5L illustrate the pre-shaped legs in a collapsed and expanded configuration, wherein the proximal and distal alignment components extend within the expandable basket.

DETAILED DESCRIPTION

It is understood that the examples below discuss uses in the airways of the lungs. However, unless specifically noted, the invention is not limited to use in the lung. Instead, the invention may have applicability in various parts of the body. Moreover, the invention may be used in various procedures where the benefits of the device are desired.

Figure 1:
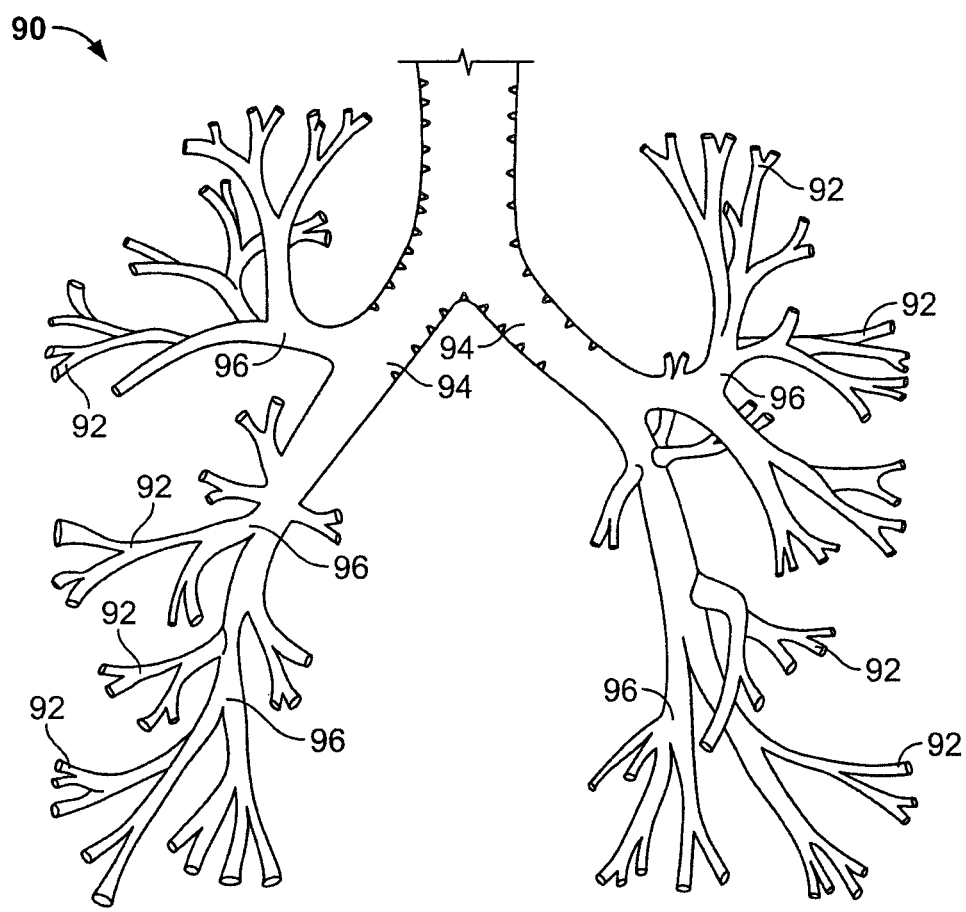
FIG. 1 is an illustration of the airways within a human lung.
Figure 2A:
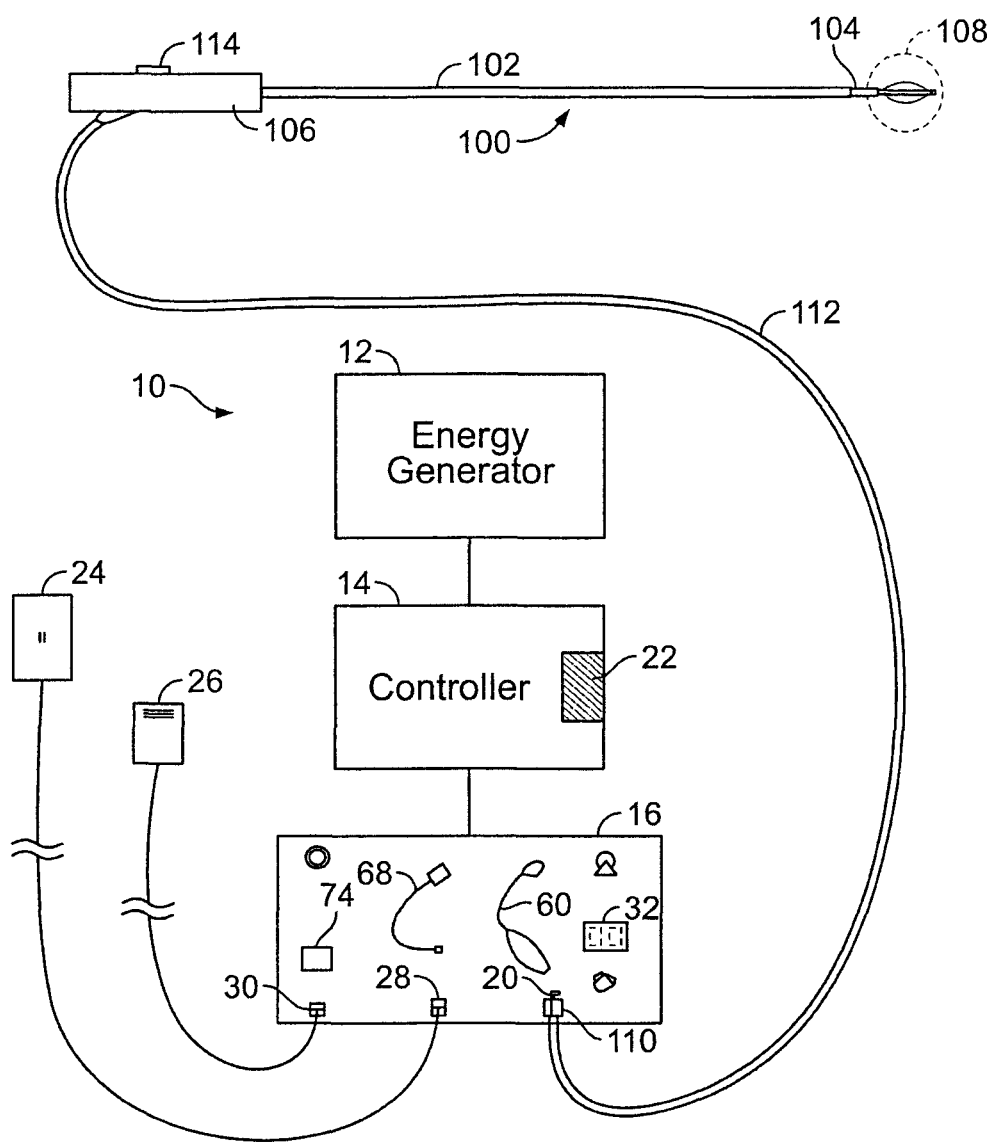
FIG. 2A is a schematic view of an exemplary system for delivering energy according to the present invention.

FIG. 2A shows a schematic diagram of one example of a system 10 for delivering therapeutic energy to tissue of a patient for use with the device described herein. The illustrated variation shows, the system 10 having a power supply (e.g., consisting of an energy generator 12, a controller 14 coupled to the energy generator, a user interface surface 16 in communication with the controller 14). It is noted that the device may be used with a variety of systems (having the same or different components). For example, although variations of the device shall be described as RF energy delivery devices, variations of the device may include resistive heating systems, infrared heating elements, microwave energy systems, focused ultrasound, cryo-ablation, or any other energy deliver system. It is noted that the devices described should have sufficient length to access the tissue targeted for treatment. For example, it is presently believed necessary to treat airways as small as 3 mm in diameter to treat enough airways for the patient to benefit from the described treatment (however, it is noted that the invention is not limited to any particular size of airways and airways smaller than 3 mm may be treated). Accordingly, devices for treating the lungs must be sufficiently long to reach deep enough into the lungs to treat these airways. Accordingly, the length of the sheath/shaft of the device that is designed for use in the lungs should preferably be between 1.5-3 ft long in order to reach the targeted airways.

The particular system 10 depicted in FIG. 2A is one having a user interface as well as safety algorithms that are useful for the asthma treatment discussed above. Addition information on such a system may be found in U.S. Provisional application No. 60/674,106, filed Apr. 21, 2005 entitled CONTROL METHODS AND. DEVICES FOR ENERGY DELIVERY, the entirety of which is incorporated by reference herein.

Referring again to FIG. 2A, a variation of a device 100 described herein includes a flexible sheath 102, an elongate shaft 104 (in this example, the shaft extends out from the distal end of the sheath 102), and a handle or other operator interface 106 (optional) secured to a proximal end of the sheath 102. The distal portion of the device 100 includes an energy transfer element 108 (e.g., an electrode, a basket electrode, a resistive heating element, cyroprobe, etc.). Additionally, the device includes a connector 110 common to such energy delivery devices. The connector 110 may be integral to the end of a cable 112 as shown, or the connector 110 may be fitted to receive a separate cable 112. In any case, the device is configured for attachment to the power supply via some type connector 110. The elongate portions of the device 102 and 104 may also be configured and sized to permit passage through the working lumen of a commercially available bronchoscope or endoscope. As discussed herein, the device is often used within an endoscope, bronchoscope or similar device. However, the device may also be advanced into the body with or without a steerable catheter, in a minimally invasive procedure or in an open surgical procedure, and with or without the guidance of various vision or imaging systems.

FIG. 2A also illustrates additional components used in variations of the system. Although the depicted systems are shown as RF type energy delivery systems, it is noted that the invention is not limited as such. Other energy delivery configurations contemplated may include or not require some of the elements described below. The power supply (usually the user interface portion 16) shall have connections 20, 28, 30 for the device 100, return electrode 24 (if the system 10 employs a monopolor RF configuration), and actuation pedal(s) 26 (optional). The power supply and controller may also be configured to deliver RF energy to an energy transfer element configured for bipolar RF energy delivery. The user interface 16 may also include visual prompts 32, 60, 68, 74 for user feedback regarding setup or operation of the system. The user interface 16 may also employ graphical representations of components of the system, audio tone generators, as well as other features to assist the user with system use.

In many variations of the system, the controller 14 includes a processor 22 that is generally configured to accept information from the system and system components, and process the information according to various algorithms to produce control signals for controlling the energy generator 12. The processor 22 may also accept information from the system 10 and system components, process the information according to various algorithms and produce information signals that may be directed to the visual indicators, digital display or audio tone generator of the user interface in order to inform the user of the system status, component status, procedure status or any other useful information that is being monitored by the system. The processor 22 of the controller 14 may be digital IC processor, analog processor or any other suitable logic or control system that carries out the control algorithms. U.S. Provisional application No. 60/674,106 filed Apr. 21, 2005 entitled CONTROL METHODS AND DEVICES FOR ENERGY DELIVERY the entirety of which is incorporated by reference herein.

Figure 2B:
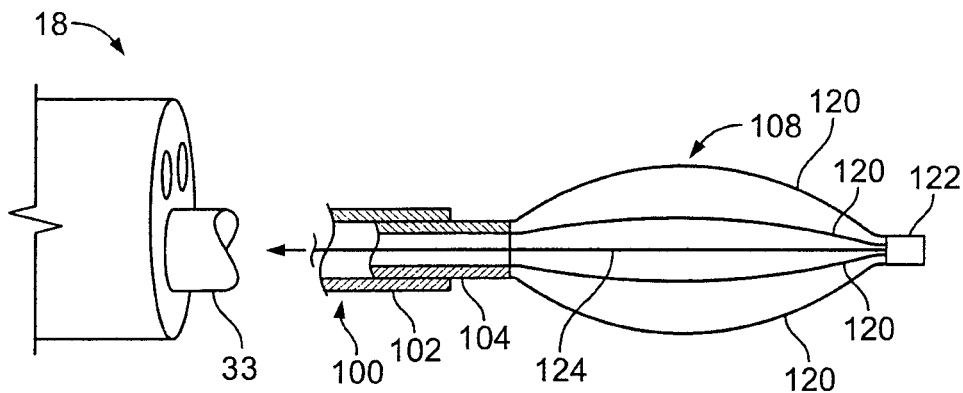
FIG. 2B is a side view of a device extending out of an endoscope/bronchoscope, where the device has an active distal end for treating tissue using energy delivery.

FIG. 2B illustrates one example of an energy transfer element 108. In this example the energy transfer element 108 is a "basket-type" configuration that requires actuation for expansion of the basket in diameter via a slide mechanism 114 on the handle 106. Such a feature is useful when the device is operated intralumenally or in anatomy such as the lungs due to the varying size of the bronchial passageways that may require treatment. As illustrated, the basket contains a number of arms 120 which carry electrodes (not shown). In this variation the arms 120 are attached to the elongated shaft 104 at a proximal end while the distal end of the arms 120 are affixed to a distal tip 122. To actuate the basket 108 a wire or tether 124 is affixed to the distal tip 122 to enable compression of the arms 120 between the distal tip 122 and elongate sheath 104.

FIG. 2B also illustrates the device 100 as being advanced through a working channel 33 of a bronchoscope 18. While a bronchoscope 18 may assist in the procedure, the device 100 may be used through direct insertion or other insertion means as well.

As noted above, some variations of the devices described herein have sufficient lengths to reach remote parts of the body (e.g., bronchial passageways around 3 mm in diameter). FIGS. 3A-3G illustrate various configurations that reduce the force required to actuate the device's basket or other energy transfer element.

Figure 3A:
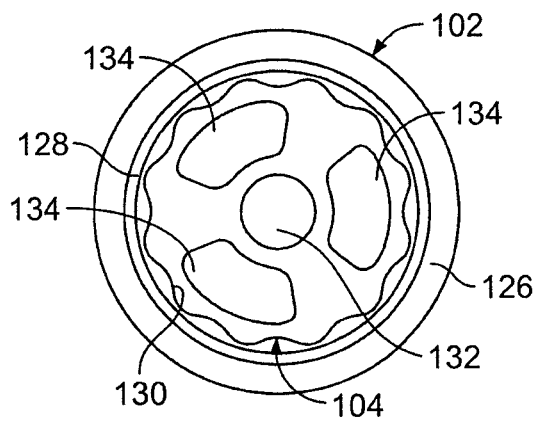
FIGS. 3A-3G show various features of the device allowing for low force deployment of the energy element.

FIG. 3A illustrates a cross section taken from the sheath 102 and elongate shaft 104. As shown, the sheath 102 includes an outer layer 126 and an inner lubricious layer 128. The outer layer 126 may be any commonly known polymer such as Nylon, PTFE, etc. The lubricious layers 128 discussed herein may comprise a lubricious polymer (for example, HDPE, hydrogel, polytetrafluoroethylene). Typically, lubricious layer 128 will be selected for optimal pairing with the shaft 104. One means to select a pairing of polymers is to maximize the difference in Gibbs surface energy between the two contact layers. Such polymers may also be chose to give the lubricious layer 128 a different modulus of elasticity than the outer layer 126. For example, the modulus of the lubricious layer 128 may be higher or lower than that of the outer layer 126.

Alternatively, or in combination, the lubricious layers 128 may comprise a fluid or liquid (e.g., silicone, petroleum based oils, food based oils, saline, etc.) that is either coated or sprayed on the interface of the shaft 104 and sheath 102. The coating may be applied at the time of manufacture or at time of use. Moreover, the lubricious layers 128 may even include polymers that are treated such that the surface properties of the polymer changes while the bulk properties of the polymer are unaffected (e.g., via a process of plasma surface modification on polymer, fluoropolymer, and other materials). Another feature of the treatment is to treat the surfaces of the devices with substances that provide anti-bacterial/antimicrobial properties.

In one variation of the invention, the shaft 104 and/or sheath 102 will be selected from a material to provide sufficient column strength to advance the expandable energy transfer element within the anatomy. Furthermore, the materials and or design of the shaft/sheath will permit a flexibility that allows the energy transfer element to essentially self-align or self-center when expanded to contact the surface of the body passageway. For example, when advanced through tortuous anatomy, the flexibility of this variation should be sufficient that when the energy transfer element expands, the shaft and/or sheath deforms to permit self-centering of the energy transfer element. Examples of shaft 104 or sheath 102 materials include nylon, PET, LLDPE, HDPE, Plexar PX, PTFE, teflon and/or any other polymer commonly used in medical devices. As described above, the inner or outer surfaces of the shaft 104 and/or sheath 102 may also comprise lubricant impregnations or coatings, such as silicone fluid, carbon, PTFE, or any of the materials described with reference to lubricous layer 128. It is noted that the other material selection and/or designs described herein shall aid in providing this feature of the invention.

FIG. 3A also depicts a variation of a shaft 104 for use in the present device. In this variation the shaft 104 includes a corrugated surface 130. It is envisioned that the corrugated surface 130 may include ribbed, textured, scalloped, striated, ribbed, undercut, polygonal, or any similar geometry resulting in a reduced area of surface contact with any adjoining surface(s). The corrugated surface 130 may extend over a portion or the entire length of the shaft 104. In addition, the shape of the corrugations may change at varying points along the shaft 104.

The shaft 104 may also include one or more lumens 132, 134. Typically, one lumen will suffice to provide power to the energy transfer elements (as discussed below). However, in the variation show, the shaft may also benefit from additional lumens (such as lumens 134) to support additional features of the device (e.g., temperature sensing elements, other sensor elements such as pressure or fluid sensors, utilizing different lumens for different sensor leads, and utilizing separate or the same lumen(s) for fluid delivery or suctioning, lumens for blowing gas (e.g., pressurized air, hot air) into the airway to move or desiccate secretions (e.g., mucus) out of the way, etc.). In addition, the lumen(s) may be used to simultaneously or sequentially deliver fluids and/or suction fluid to assist in managing the moisture within the passageway. Such management may optimize the electrical coupling of the electrode to the tissue (by, for example, altering impedance).

Since the device is suited for use in tortuous anatomy, a variation of the shaft 104 may have lumens 134 that are symmetrically formed about an axis of the shaft. As shown, the additional lumens 134 are symmetric about the shaft 104. This construction provides the shaft 104 with a cross sectional symmetry that aid in preventing the shaft 104 from being predisposed to flex or bend in any one particular direction. Further, the shaft 104 may be designed to increase clearance between a center wire 124 that runs through the shaft lumen 132 so as to minimize friction and improve basket 108 deployment in tortuous anatomy. Still further, the shaft 104 may be designed so as to efficiently transmit torque from the handle 106 to the basket array 108 in order to rotate the basket array 108 within the airways so as to enhance device positioning. For example, this may be accomplished by incorporating a braided member (e.g., braided wire) into the shaft 104 extrusion or by joining the shaft 104 coaxially with the braided member.

Figure 3B:
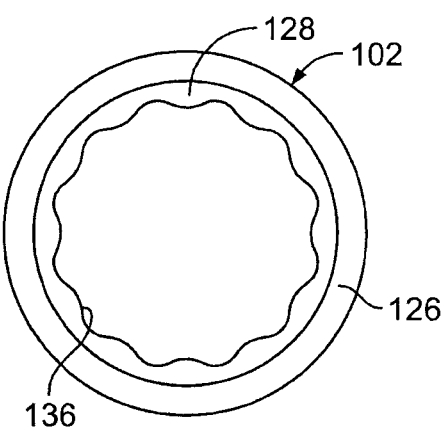

FIG. 3B illustrates another variation where the sheath 102 includes an outer layer 126 and a lubricious layer 128. However, in this variation the lubricious layer 128 also includes a corrugated surface 136. It is noted that any combination of the sheath 102 and shaft 104 may have a corrugated surface.

Figure 3C:
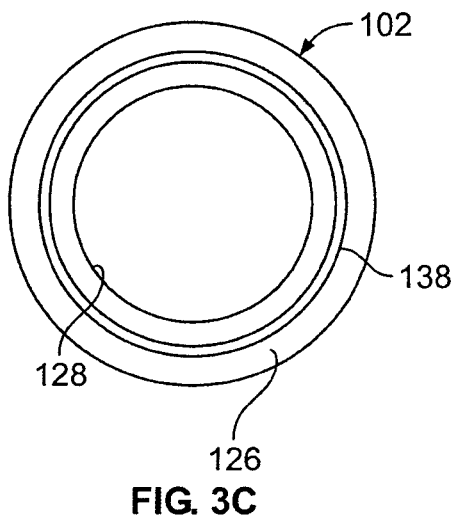

FIG. 3C illustrates yet another aspect of construction of a sheath 102 for use with the present device. In this variation, the sheath 102 includes a multi-layer construction having an outer layer 126, one or more middle layers 138. The middle layers 138 may be selected to have properties that transition between the outer layer properties and the lubricious layer properties, and improve the bonding between inner and outer layer. Alternatively, the middle layer 138 may be selected to aid in the column strength of the device. An example of the middle layer includes LLDPE, Plexar PX 306, 3060, and/or 3080.

Figure 3D:
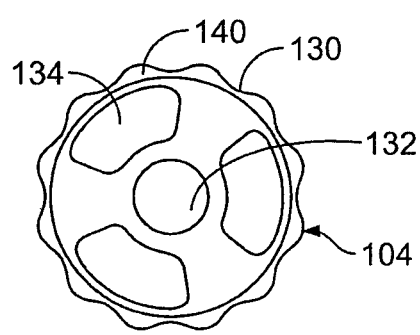
Figure 3E:
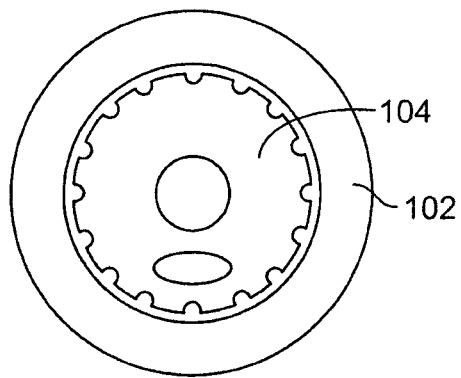
Figure 3F:
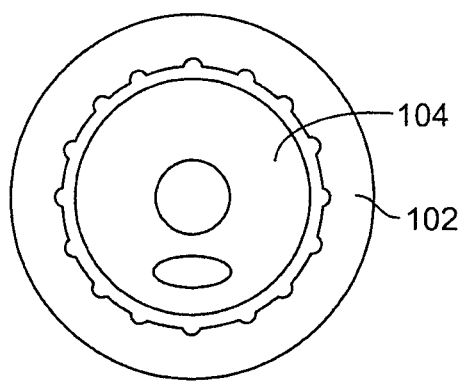
Figure 3G:
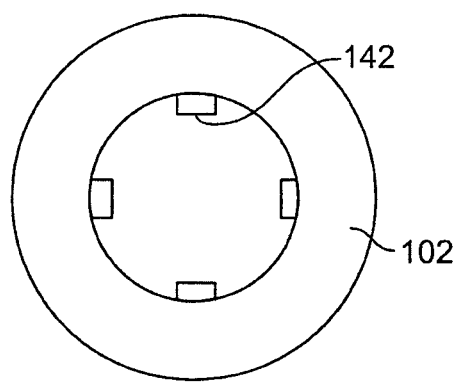

FIG. 3D depicts a variation of a shaft 104 for use with the devices described herein where the shaft outer surface comprises a lubricious layer 140. As illustrated, the shaft outer surface may also optionally have a corrugated surface 130. FIGS. 3E-3G illustrate additional variations of corrugated surfaces. As shown in FIGS. 3E and 3F, either or both the sheath 102 and the shaft 104 may have corrugated surfaces that are formed by interrupting the surface. Naturally, different shapes and configurations may be otherwise constructed. FIG. 3G illustrates a variation where the sheath 102 comprises protrusions or spacer 142 to separate the surfaces of the sheath/shaft.

FIGS. 3H and 3I illustrate further variations of a shaft 104 which may be incorporated within any of the devices described herein. FIG. 3H illustrates a two lumen shaft 104 having an oblong or oval shaped cross section. The first lumen 132 may be utilized to receive the conductive center wire 124 which electrically couples the legs 120 to the energy generator 12. The second lumen 134 may be utilized to receive temperature detecting leads 172 as described in more detail with reference to FIG. 7C. Further, a coil 135 or other reinforcing element (e.g., polymeric insert, braided member) may be utilized to prevent kinking or collapse of the shaft 104, which is of particular benefit during basket 108 deployment in tortuous anatomy. In this depiction, the coiled wire 135 is disposed within lumen 132 of the shaft 104 and surrounding the center wire 124. Referring now to FIG. 3I, a single lumen shaft 104 having a D-shaped cross section is illustrated. The single lumen 132 receives the center wire 124 as in FIG. 3H, but in this embodiment the reinforcing coil 135 is disposed outside the shaft 104 and further encompasses the temperature detecting leads 172. The coil 135 may also reinforce a tubular sheath 102 which is disposed over the coil 135 and extends along a length of the shaft 104. The embodiments of FIGS. 3I and 3H also provide an exposed basket 108 configuration (e.g., sheathless) which reduces friction and as such improves basket 108 deployment mechanics.

These oblong, oval, or D-shaped shaft cross sections advantageously allow for a reduced profile while still axially centering the center wire 124 with respect to the expandable basket 108. This reduced size profile not only permits passage of the sheathless catheter of FIG. 3H or sheathed catheter of FIG. 3I through the working channel lumen of an access device, such as a bronchoscope, but allows for fluid delivery or suction through an opening created between the working channel lumen and an outer surface of the catheter.

As already described above, alternatively or in the adjunct, additional lumens 134 within the device shaft 104 may be utilized for fluid delivery of cleaning fluids (e.g., saline, bio-compatible fluids), drugs (e.g., lidocane, tetracaine), cooling fluids (e.g., cooled saline, cooled sterile water, or other fluids for cooling the airway wall), electrically conductive fluids (e.g., saline), thermally conductive fluids, or fluids to increase the viscosity of mucus so it can be more easily suctioned (e.g., saline), or for suctioning of delivered fluids or excretions within the airway (e.g., mucus). Advantageously, suctioning or fluid delivery from or to the airway may be accomplished while the asthma treatment device remains within the airways without requiring the device user to pull the device out of the airway, which in turn reduces procedure time and improves patient manageability. For example, irrigation and/or suctioning may be carried out simultaneously or sequentially with energy delivery to the airway wall while the device is within the airway.

Figure 4C:
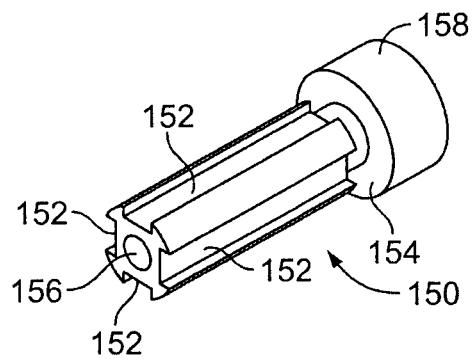
Figure 4C:
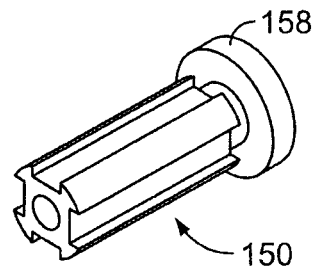
Figure 4C:
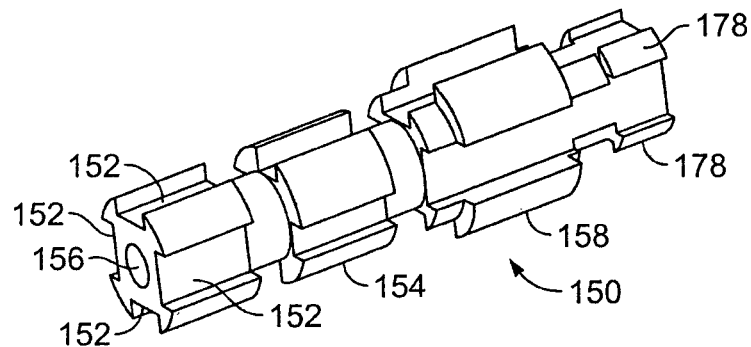

FIGS. 4A-4D illustrate yet another feature that may be incorporated with any of the subject devices. FIG. 4A illustrates an example of an alignment component 150. In this variation, the alignment component 150 includes a plurality of seats 152 that nest electrode arms (not shown). As discussed herein, the seats 152 allow for improved control of the angular spacing of the arms. Moreover, the seats 152 permits design of a device in which the flexure length of each of the arms of a basket type device is uniform (even if the tolerance of each arm varies). Though the alignment component 150 is shown as having four seats 152, any number of seats may be employed.

The alignment component 150 also includes a stop 154. The stop 154 acts as a reference guide for placement of the arms as discussed below. In this variation, the stop 154 is formed from a surface of an end portion 158. This end portion 158 is typically used to secure the alignment component 150 to (or within) the sheath/shaft of the device. The alignment component 150 may optionally include a through hole or lumen 156.

FIG. 4B illustrates another variation of an alignment component 150. This variation is similar to the variation shown in FIG. 4A, with the difference being the length of the end portion 158. The smaller end portion 158 may optionally be employed when the component 150 is used at the distal end of the device. In such a case, the component 158 may not be attached to the sheath or shaft. In addition, the end portion 158 may optionally be rounded, for example, to minimize tissue trauma that may be caused by the end of the device.

The alignment components 150 of the present invention may be fabricated from a variety of polymers (e.g., PEEK, ULTEM, PEI, nylon, PET and/or any other polymer commonly used in medical devices), either by machining, molding, or by cutting an extruded profile to length. One feature of this design is electrical isolation between the legs, which may also be obtained using a variation of the invention that employs a ceramic material for the alignment component. However, in one variation of the invention, an alignment component may be fabricated from a conductive material (e.g., stainless steel, polymer loaded with conductive material, or metallized ceramic) so that it provides electrical conductivity between adjacent electrode legs and the conductive wire. In such a case, a power supply may be coupled to the alignment component, which then electrically couples all of the legs placed in contact with that component. The legs may be attached to the conductive alignment component with conductive adhesive, or by soldering or welding the legs to the alignment component. This does not preclude the legs and alignment component form being formed from one piece of metal.

Devices of the present invention may have one or more alignment components. Typically the alignment components are of the same size and/or the angular spacing of the seats is the same. However, variations may require alignment components of different sizes and/or different angular spacing. Another variation of the invention is to have the seats at an angle relative to the axis of the device, so as to form a helically shaped energy delivery element.

FIG. 4C illustrates another variation of an alignment component 150. In this variation, the alignment component 150 includes four seats 152. This variation includes an alignment stop 154 that protrudes from the surface of the component 150. In addition, the end portion 158 of the alignment component 150 is also of a cross section that may improve strength of the connection between the component and the sheath/shaft. In this case, the end portion 158 allows for crimping of the sheath/shaft. Optionally as shown, radial protrusions 178 at the right of the end portion 158 may be included to allow heat bonding of the alignment component to the shaft. In this case, the shaft may be a polymer with a melting temperature lower than that of the alignment component. When constrained to be coaxial, heat, and if necessary axial pressure, may be applied to join the two components.

Figure 4D:
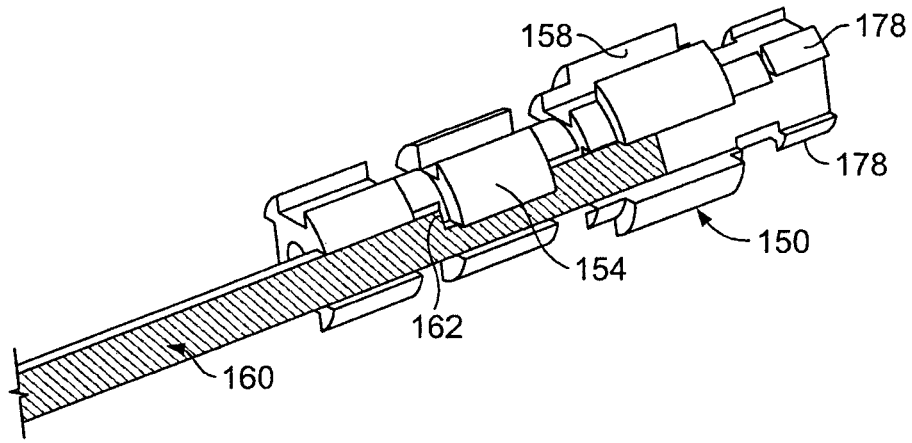
FIGS. 4D-4E demonstrate the alignment components coupled to a leg of the device.

FIG. 4D illustrates the protrusion-type stop 154 that retains a notch 162 of the electrode leg 160. This mode of securing the electrode leg 160 provides a "redundant-type" joint. In one example, the leg 160 is secured to the alignment component 150 using a sleeve (not shown) placed over both the leg 160 and alignment component 150 with or without the use of an adhesive within the sleeve. The notch 162 in the leg 160 is placed around the protrusion-type-stop 154. As a result, the notch-stop interface prevents the leg from being pulled from the device and is especially useful to prevent the proximal or near ends of the legs from separating from the device. It is noted that this safety feature is especially important when considering that if the proximal/near ends of the legs separate and hook on the anatomical passage, it may be difficult or impossible to remove the device from the passage. Such a failure may require significant medical intervention.

Figure 4E:
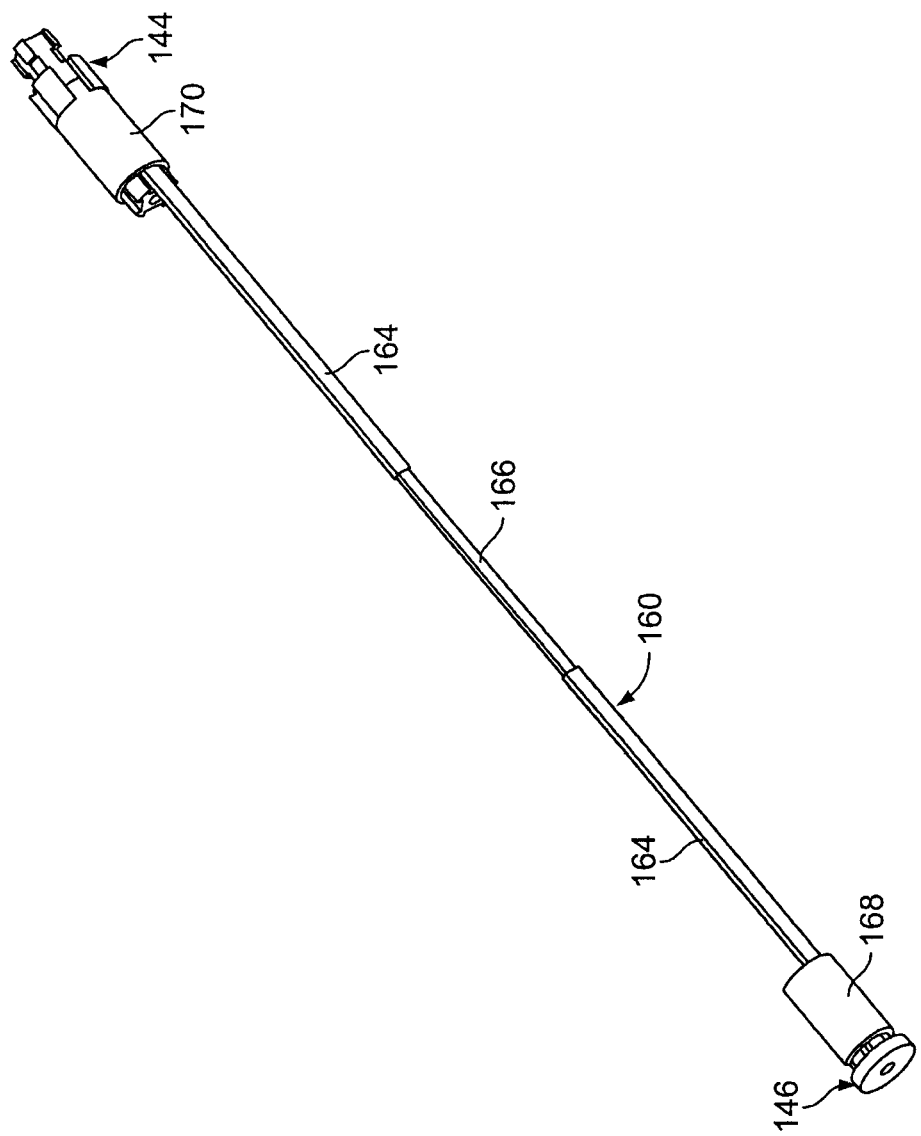

FIG. 4E illustrates one example of a leg 160 affixed to near/proximal and far/distal alignment components 144, 146. As shown, the leg 160 may have an insulated portion 164 and an exposed portion 166 that form electrodes. The near and far ends of the leg 160 are secured to respective alignment components 144, 146. In this example, sleeves 168 and 170 cover the leg and alignment component. As noted above, one or both of the alignment components may be electrically conductive to provide power to the electrodes. Furthermore, adhesive (e.g., cyanoacrylate (e.g., loctite), UV-cured acrylic, epoxy, and/or any such adhesive) may also be used to secure the leg and/or sleeves to the components.

Figure 4F:
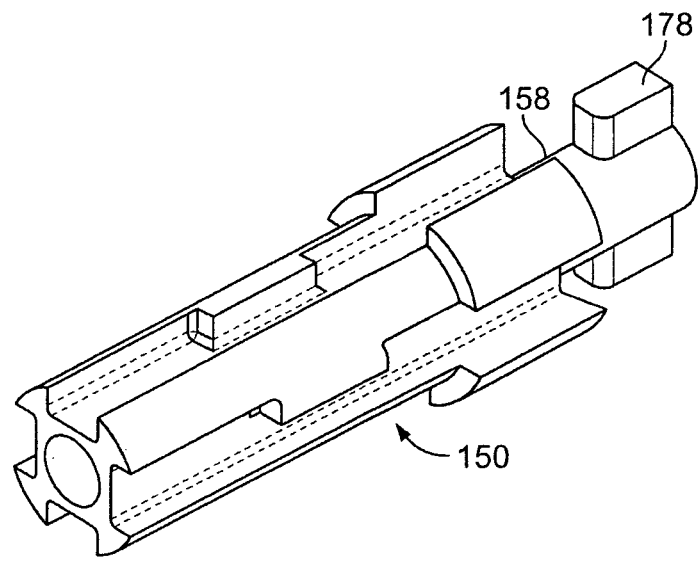
FIGS. 4F-4H illustrate an additional variation of an alignment component.
Figure 4G:
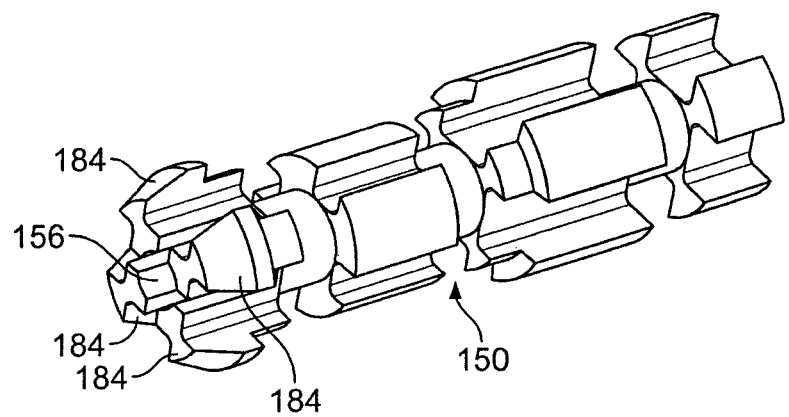
Figure 4H:
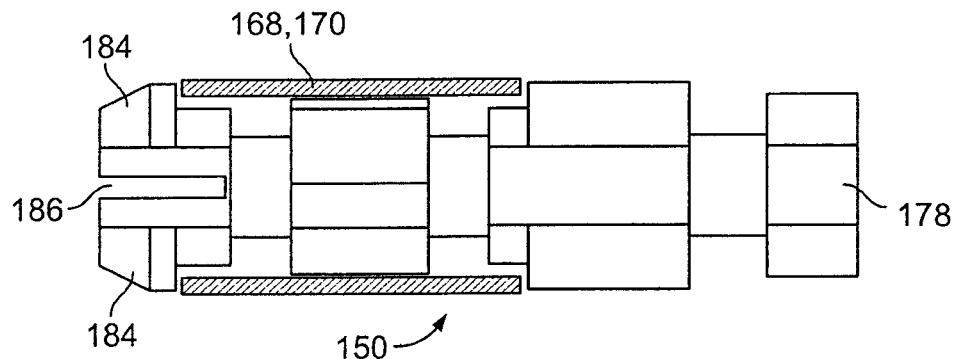

Additionally, the alignment components may be designed such that the sleeves 168, 170 may be press or snap fit onto the alignment components, eliminating the need for adhesively bonding the sleeves to the alignment components. FIG. 4F illustrates a perspective view of an end portion of an alignment component 150 having one or more slots 186 to create end portion segments 184. The slots 186 permit deflection of the end portion segments 184 to allow sliding of a sleeve or hypotube (either a near or far sleeve 168 or 170) over the end portion. FIG. 4G shows a cross sectional view of the component 150 of FIG. 4F. As shown, once advanced over the end portion segment 184, the sleeve or hypotube becomes secured to the component 150. To lock the sleeve in place, an insert or wire member 124 (not shown) is placed in the through hole or lumen 156. The insert or wire member prevents inward deflection of the end portion segments 184 thereby ensuring that the sleeve or hypotube remains secured to the component 150.

Figure 4I:
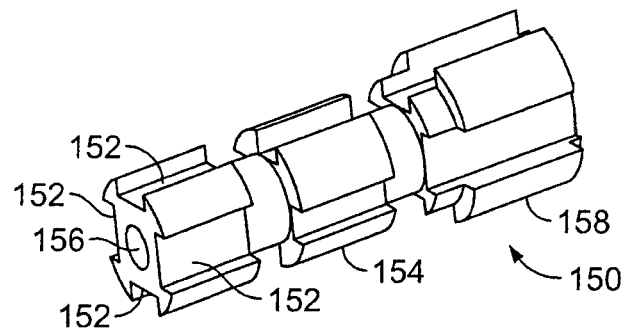
FIG. 4I illustrates yet another variation of an alignment component.

Referring now to FIG. 4I, another variation of the alignment component 150 is shown. This proximal joint 150 is similar to that of FIG. 4C, but has a reduced axial length by omission of the radial protrusions 178. This shortening improves joint flexibility in tortuous airways as a user can translate the shaft 104 and basket assembly 108 with more ease through the sheath 102 which in turn improves basket 108 deployment. In this embodiment, the end portion 158 may be directly coupled to the shaft 104 by utilizing heat shrink (e.g., PET) with a wicking adhesive as described above. This coupling results in a lower proximal joint profile so as to reduce the friction between the sheath 102 and shaft 104 which in turn improves joint 150 flexibility and basket 108 deployment. Further, in this embodiment, a PET shaft 104 may be utilized to provide enhanced pushability of the shaft 104 so as to further aid in basket 108 deployment and to reduce susceptibility to water absorption so as to ensure greater consistency of deployed basket diameter (e.g., >10 mm).

Figure 4J:
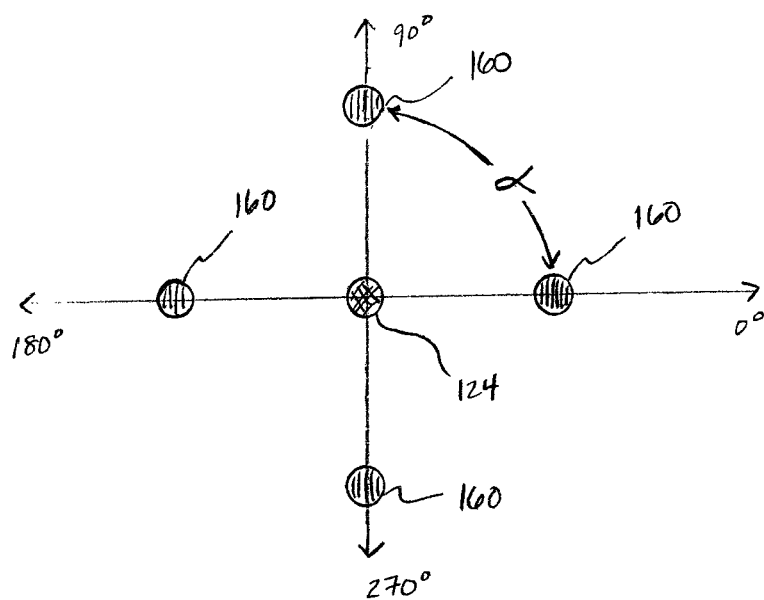
FIG. 4J illustrates an angle between basket electrode legs.

As discussed herein, the seats 152 allow for improved control of the angular spacing of the legs 160. In particular, the seats 152 of the proximal and distal alignment components 144, 146 are aligned, wherein the angle between adjacent legs 160 is determined by the angle between adjacent seat 152. The seats 152 preferably provide for symmetrical deployment of the arms 160, wherein any angle between adjacent legs varies less than 20 degrees. As shown in cross sectional view of FIG. 4J, in the case of a four leg basket 108, the angle $\alpha$ between adjacent legs is in a range from about 70 degrees to about 110 degrees, preferably 90 degrees. Likewise, in the case of a six leg basket 108, the angle between adjacent legs is in a range from about 45 degrees to about 75 degrees, preferably 60 degrees so that a variance is less than 15 degrees. Further, in the case of a eight leg basket 108, the angle between adjacent legs is in a range from about 33 degrees to about 57 degrees, preferably 45 degrees so that a variance is less than 12 degrees or for a ten leg basket 108, the angle between adjacent legs is in a range from about 26 degrees to about 46 degrees, preferably 36 degrees so that a variance is less than 10 degrees. Symmetrical deployment ensures proper temperature distribution, which may be important for the treatment of asthma in the lung airways. It will be appreciated that the present invention is not limited to an even number of basket legs 160. For example, five or seven basket legs 160 may be employed as long as the spacing between each leg 160 is equivalent.

Figure 5A:
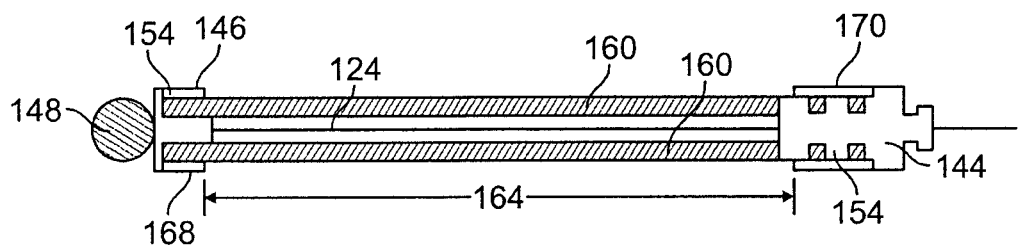
FIGS. 5A-5B is a variation of an energy transfer element according to the present device.

FIG. 5A shows a cross sectional view of two legs 160 attached to alignment components 144, 146. The sheath and shaft have been omitted for clarity. The flexure length 164 of the leg 160 is defined as the length between the alignment components 144, 146 over which the leg may flex when the proximal and distal ends are moved closer to one another. As noted above, the alignment components permit the flexure length 164 of the legs 160 to be uniform even if the leg lengths vary. The flexure length 164 is essentially set by the longest leg, the shorter legs may float between the stops 154 of the alignment components 144, 146. As an additional measure to prevent the legs 160 from inverting, the lengths of the sleeves 168 and 170 may be selected to be less than the length of the respective alignment components 144, 146 (as shown in the figure). The tendency of the leg to deflect outward can be improved by selecting the sleeve length as such. When the legs 160 expand they are supported by their respective seat on the interior side but unsupported on outer side. In yet another variation, the seats can slant to predispose the arms to deflect in a desired direction. For example, as shown in FIG. 5C, the seats 152 can slant as shown to predispose the legs 160 to outward deflection. Such a construction can be accomplished by machining or by drafting a molded part in the direction of the catheter axis. As shown in FIG. 5D, the leg can have a slight bend or shape that predisposes the legs to bow outward.

Figure 5B:
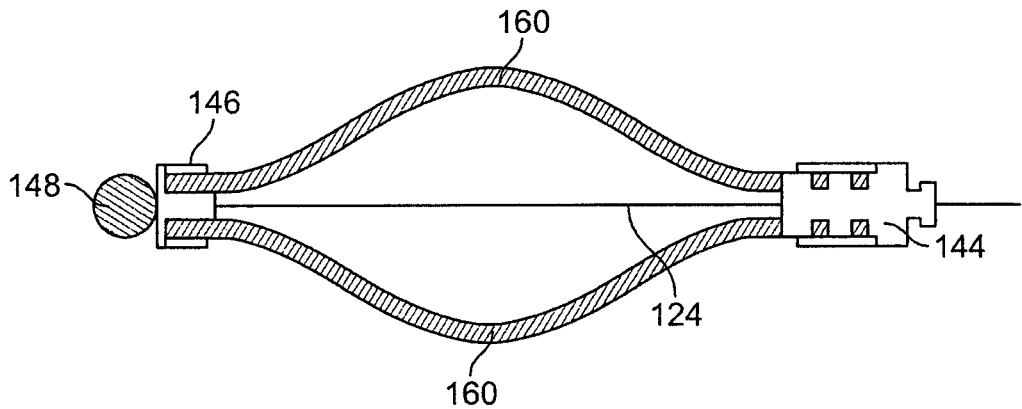
Figure 5C:
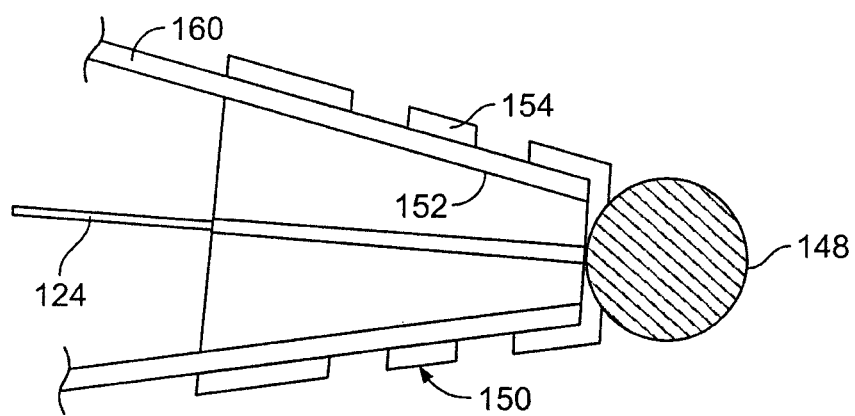
FIGS. 5C-5D show variations in which the legs of the device are biased to expand outward.
Figure 5D:
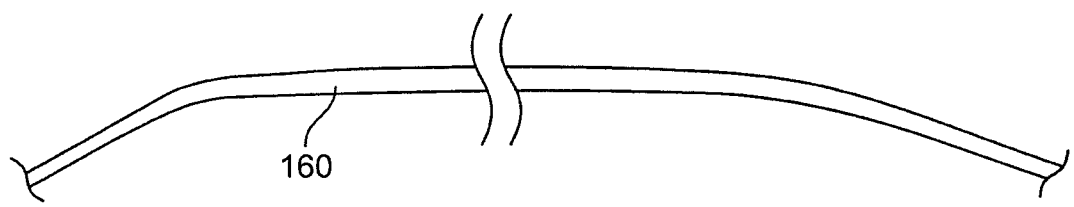

FIG. 5B illustrates the variation of FIG. 5A in an expanded state. As shown, the device may have a wire 124 or other similar member that permits movement of the far alignment component 146 relative to the near alignment component 144. As noted herein, the wire 124 may be electrically conductive to provide power to electrodes on the device. FIG. 5B also illustrates a ball tip 148 at the end of the device. The ball tip 148 may serve as a means to secure the wire 124 as well as providing an atraumatic tip for the device.

Variations of the wire 124 may include a braided or coiled wire. The wire may be polymer coated or otherwise treated to electrically insulate or increase lubricity for easier movement within the device.

To expand the energy transfer element 108, the wire 124 may be affixed to a handle 106 and actuated with a slide mechanism 114 (as shown in FIG. 2A.) In an alternative design, the wire 124 may be affixed between the handle 106 and the distal end of the energy transfer element 108. In such a case, the slide mechanism 114 may be affixed to the shaft 104. Movement of the slide mechanism 114 causes expansion of the element 108 as the shaft 104 causes movement of the proximal end of the energy transfer element (being fixed to the shaft) relative to the distal end of the energy transfer element (being fixed to the wire 124). In an additional variation, movement of the slide 114 may have two outcomes: 1) advancing the energy transfer element out of the sheath; and 2) subsequently expanding the energy transfer element. Such constructions are disclosed in U.S. patent application Ser. No. 09/436,455 filed Nov. 8, 1999 the entirety of which is incorporated by reference herein. In a still further variation, movement of the slide 114 may cause the wire 124 to be pulled proximally while the shaft 104 is pushed distally so that energy transfer element remains stationary during deployment.

Figure 5E:
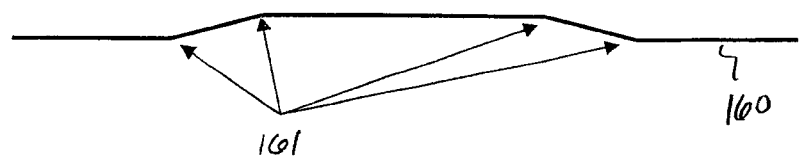
FIGS. 5E-5F illustrate another variation of the leg having a pre-shaped form.
Figure 5F:
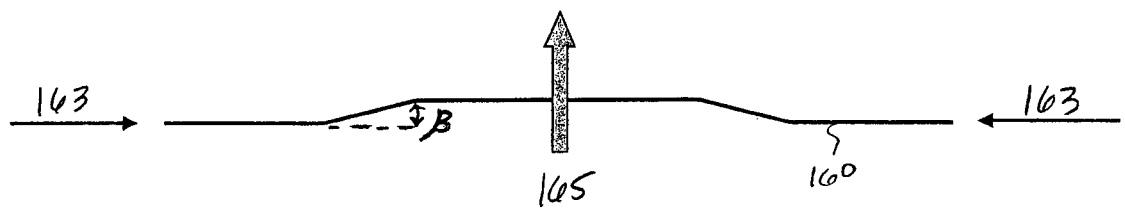

Referring now to FIGS. 5E-5N, the electrode legs 160 may be pre-shaped as already described herein. In particular, the electrodes 160 may be pre-shaped so as to control the direction in which the legs deflect upon basket deployment 108 so as to prevent electrode inversion, provide controlled buckling of the basket electrode 108, and improve tissue contact. FIG. 5E illustrates a pre-bent leg 160 having four discrete bends 161. As shown in FIG. 5F, when axial compressive loads 163 are applied to the electrode 160 during deployment, the pre-shaped leg is predisposed to buckle or deflect in a predictable, desired outwards direction 165 to make contact with the airway wall. Hence, the pre-shaped leg 160 provides for preferential buckling in the outward direction 165, which is of particular benefit in tortuous airways where orthogonal or side loads commonly cause leg inversions. As illustrated in the example of FIG. 5F, an angle of the discrete pre-bends 161 on the proximal and distal ends of the electrode 160 may be at an angle that is in a range from about 10 degrees to about 20 degrees, preferably 15 degrees.

Figure 5G:
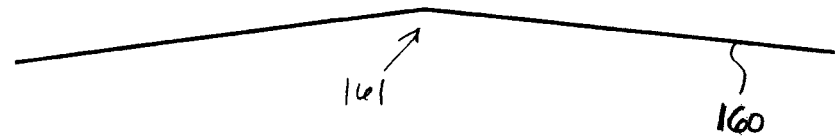
FIGS. 5G-5I show further variations of the pre-bent legs.
Figure 5H:
Figure 5I:
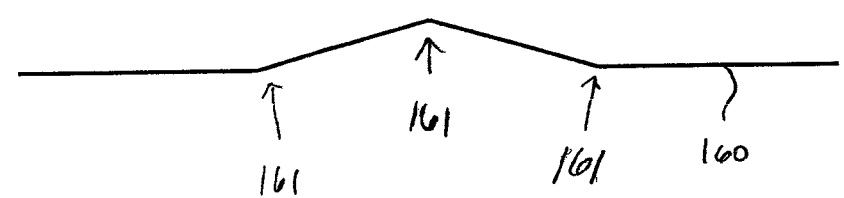
Figure 5M:
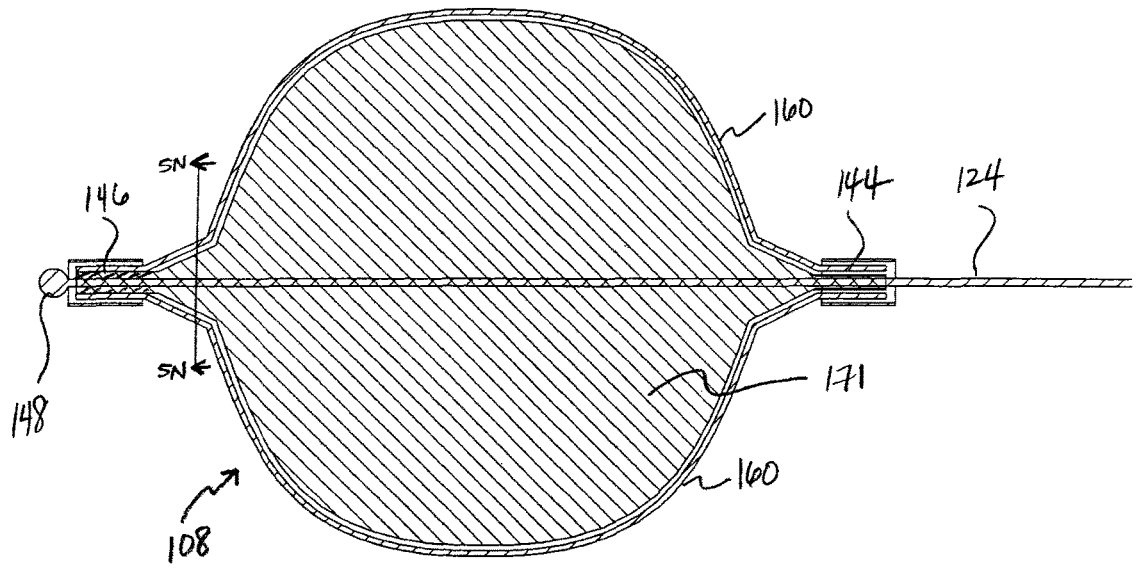
FIGS. 5M-5N illustrate the pre-shaped legs in an expanded configuration, wherein a basket support is disposed within the expandable basket.
Figure 5N:
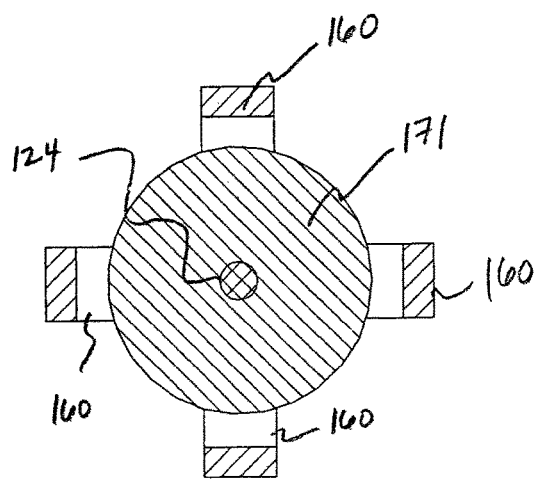

It will be appreciated that several other pre-shaped variations may be employed to induce buckling in the desired outward direction 165. For example, the pre-bent electrode may comprise a single bend 161 as shown in FIG. 5G, two bends 161 as shown in FIG. 5H, three bends 161 as shown in FIG. 5I, and the like. Further, the angle β of the bend 161 or the positioning of the bend 161 may vary depending on a variety of factors. Still further, the electrode 160 may be pre-shaped to form a continuous curve, as illustrated in FIG. 2B, or a parabolic curve as illustrated below in FIG. 6A, or some other pre-shaped configuration in which a portion of the electrode 160 is out-of-plane from the axially active compressive loads 163.

Referring now to FIGS. 5J-5L, cross sectional views of the pre-bent legs 160 attached to proximal and distal alignment components 144, 146 are illustrated. The shaft 102 in this depiction has been omitted for clarity. In this particular embodiment, the alignment components extend within the expandable basket 108, as illustrated by reference numerals 144 a, 146 a. As the basket is deployed, as shown in FIG. 5L, the proximal and distal extrusions or flanges 144 a, 146 a in the basket 108 further prevent against electrode leg 160 inversions from the desired outward direction 165.

In addition or alternatively, inward leg buckling or inversions may also be prevented by disposing basket support(s) inside the expandable basket 108. For example, as shown in the cross sectional view of FIGS. 5M and 5N, a balloon member 171 may also be deployed inside the basket 108 and inflated to prevent inward deflection of the electrode legs 160. Further, the balloon member 171 may utilize its inflation lumen to receive cooling fluids so as to cool the electrode 160 and airway wall. Still further, the balloon member 171 may also be utilized to deploy the basket 108 in lieu of the pull wire 124.

Figure 6A:
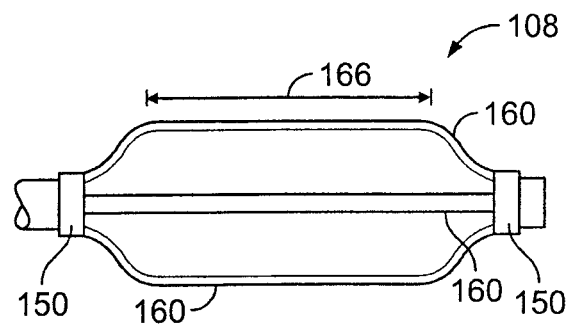
FIGS. 6A-6C show various basket configurations for the device.

FIG. 6A illustrates a variation of an energy transfer element 108 in which the legs 160 have a pre-determined shape. This shape may be selected as required for the particular application. As shown, the predetermined shape provides a certain length of the electrode 166 that may be useful for treatment of a long section of tissue.

Figure 6B:
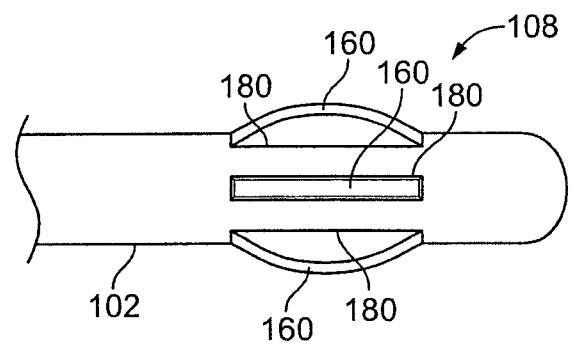

FIG. 6B illustrates another variation of the energy transfer element 108. In this variation, the legs 160 extend out of openings 180 in the sheath 102 (in other variations, the legs may extend out of openings in the shaft). Accordingly, the alignment components and other parts of the device would be located within the sheath 102.

Figure 6C:
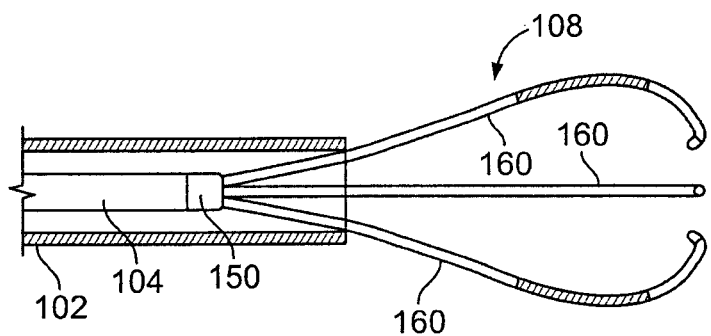

FIG. 6C illustrates yet another variation of an energy transfer element 108. In this variation, the basket is connected at a proximal end and opened at a distal end. The electrode legs 160 only have a single alignment component 150. The conductive member (or wire) may be located within the shaft 104. In this variation, advancement of the energy transfer element 108 out of the sheath 102 causes expansion of the element. The energy transfer elements may be predisposed or spring loaded to bow outward when advanced from the sheath.

Figure 7A:
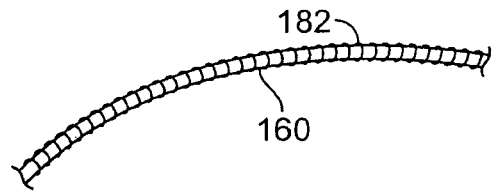
FIGS. 7A-7D illustrate various features of variations of legs for use with the present devices.
Figure 7B:
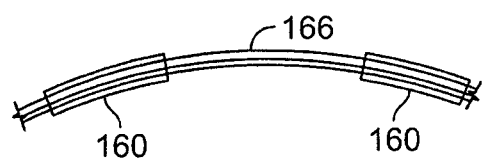

FIG. 7A illustrates an example of a leg 160 with an energy element 180 coiled around the leg 160. In this example, the energy element 182 uses conductive heating and comprises a resistance heating element coiled around the leg 160. FIG. 7B illustrates a variation of the invention having an RF electrode attached to the basket leg 160. The RF electrode may be attached to the basket leg 160 via the use of a fastener. For example, the electrode may be attached via the use of a heat shrink fastener, (e.g., polymeric material such as PET or polyethylene tubing). Alternatively, as discussed above, the entire leg may be a conductive medium where a non-conductive coating insulates the majority of the leg leaving the electrode portion uninsulated. Further examples of energy transfer element configurations include paired bipolar electrodes, where the pairs are leg to leg or within each leg, and large matrices of paired electrodes affixed to a variety of expanding members (balloons, mechanisms, etc.)

Figure 7C:
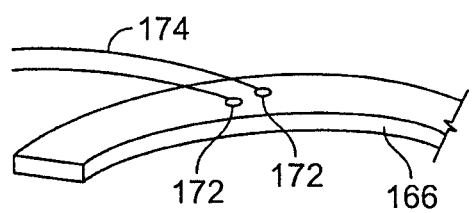

FIG. 7C illustrates a variation of the invention having thermocouple leads 172 attached to an electrode 166 or leg of the device. The leads may be soldered, welded, or otherwise attached. This variation of the invention shows both leads 172 of the thermocouple 174 attached in electrical communication to a leg 160 at separate joints (or the leads may be separated but the solder on each connection actually flows together). In this case, the temperature sensor is at the surface of the leg. This variation provides a safety measure in case either joint becomes detached, the circuit will be open and the thermocouple 174 stops reading temperature. Such a condition may be monitored via the power supply and allow a safe shutdown of the system.

By spacing the leads of the thermocouple closely together to minimize temperature gradients in the energy transfer element between the thermocouple leads, thermoelectric voltage generated within the energy transfer element does not compromise the accuracy of the measurement. The leads may be spaced as close together as possible while still maintaining a gap so as to form an intrinsic junction with the energy transfer element. In another variation of the device, the thermocouple leads may be spaced anywhere along the tissue contacting region of the energy transfer element. Alternatively, or in combination, the leads may be spaced along the portion of an electrode that remains substantially straight. The intrinsic junction also provides a more accurate way of measuring surface temperature of the energy transfer element, as it minimizes the conduction error associated with an extrinsic junction adhered to the device.

The thermocouple leads may be attached to an interior of the leg or electrode. Such a configuration protects the thermocouple as the device expands against tissue and protects the tissue from potential trauma. The device may also include both of the thermocouple leads as having the same joint.

The devices of the present invention may use a variety of temperature sensing elements (a thermocouple being just one example, others include, infrared sensors, thermistors, resistance temperature detectors (RTDs), or any other component capable of detecting temperatures or changes in temperature). The temperature detecting elements may be placed on a single leg, on multiple legs or on all of the legs.

Figure 8A:
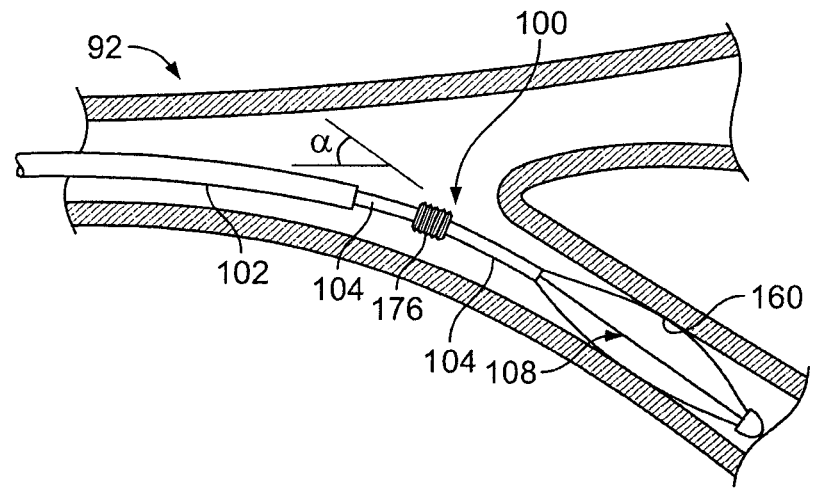
FIGS. 8A-8D show various junctions for use with the present devices to improve alignment when the device is advanced through tortuous anatomy.

The present invention may also incorporate a junction that adjusts for misalignment between the branching airways or other body passages. This junction may be employed in addition to the other features described herein. FIG. 8A illustrates a device 100 having such a junction 176 allowing alignment of the device to closely match the alignment of the airway. It is noted that the present feature also benefits those cases in which the pathway and target site are offset as opposed to having an angular difference.

The junction 176 helps to eliminate the need for alignment of the axis of the active element 108 with the remainder of the device in order to provide substantially even tissue contact. The junction may be a joint, a flexure or equivalent means. A non-exhaustive listing of examples is provided below.

Figure 7D:
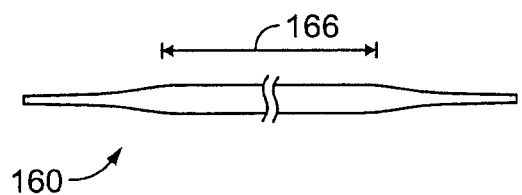

The legs 160 of the energy transfer element may have various shapes. For example, the shapes may be round, rounded or polygonal in cross section. Additionally, each leg may change cross section along its axis, providing for, for example, electrodes that are smaller or larger in cross section that the distal and proximal portions of each leg. This would provide a variety of energy delivery characteristics and bending profiles, allowing the design to be improved such that longer or wider electrode configurations can be employed. For example, as shown in FIG. 7D, if the cross-sectional thickness of the electrode portion 166 of the leg 160 is greater than the cross-sectional thickness of the distal and proximal portions of the leg, the leg would be predisposed to bow outward in the distal and proximal sections, while remaining flatter in the electrode area of the leg, potentially providing improved tissue contact.

As for the action the junction enables, it allows the distal end of the device to self-align with the cavity or passageway to be treated, irrespective of the alignment of the access passageway. FIG. 8A illustrates an example of where the access passageway and passageway to be treated are misaligned by an angle α. In the example shown in FIG. 8B, the misalignment angle α is greater than the angle illustrated in FIG. 8A. Yet, the energy transfer element 108 of the treatment device 100 remains substantially aligned with the target area.

Figure 8B:
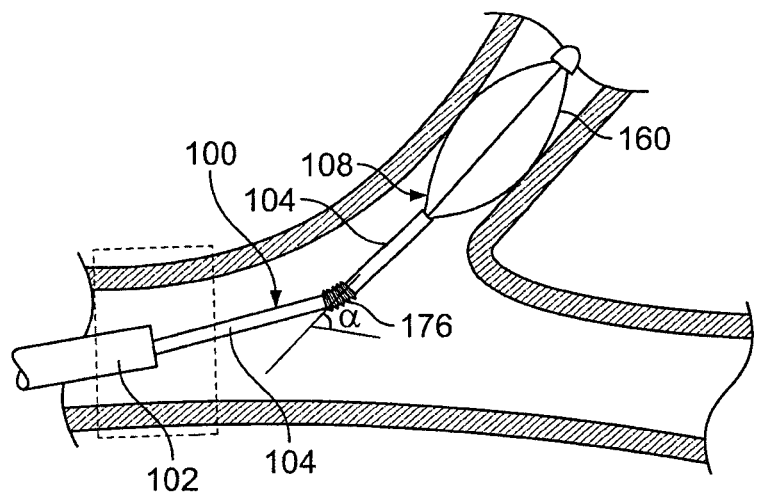
Figure 8C:
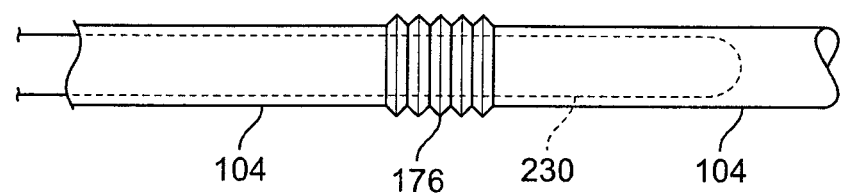
Figure 8D:
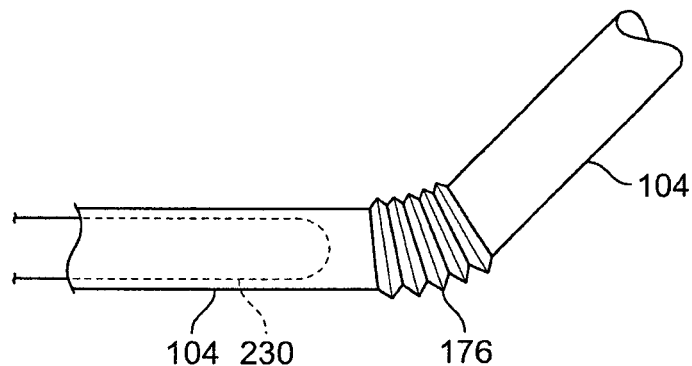

FIGS. 8C and 8D illustrate an additional variation of the junction 176. In this variation the junction 176 may be reinforced with a reinforcing member 230. The reinforcing member may have some degree of flexibility to navigate the tortuous anatomy, but the flexibility will be less than the junction 176. As shown in FIG. 8C, the reinforcing member 230 maintains the device shaft 104 in an aligned position, preferably for insertion, removal, and or navigation of the device. When desired, the reinforcing member 230 may be removed from the junction 176 as illustrated in FIG. 8D. Accordingly, upon removal, the device is free to flex or orientate as desired. Furthermore, the reinforcing member may be reinserted within the junction 176 when repositioning or removing the device from the target site. In additional variations, it is contemplated that the reinforcing member may be placed external to the device/junction.

Figure 9A:
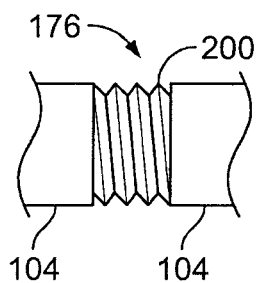
FIGS. 9A-9J are addition variations of junctions.
Figure 9B:
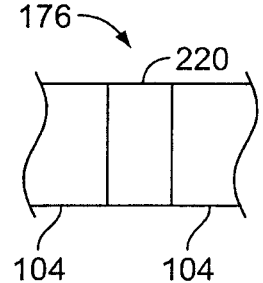

FIGS. 9A-9I illustrate additional junctions for use in the devices described herein. As for these examples, FIG. 9A illustrates a junction 176 in the form of a plurality of turns or coils 200 of a spring. The coil offers a flexure with 3-dimensional freedom allowing realignment of the active end of the subject device in any direction. Of course, a simple hinge or universal joint may also be employed.

The length of the junction (whether a spring junction or some other structure) may vary. Its length may depend on the overall system diameter. It may also depend on the degree of compliance desired. For example, with a longer effective junction length (made by extending the coil with additional turns), the junction becomes less rigid or more "floppy".

In any case, it may be desired that the junction has substantially the same diameter of the device structure adjacent the junction. In this way, a more atraumatic system can be provided. In this respect, it may also be desired to encapsulate the junction with a sleeve or covering if they include open or openable structures. Junction 176 shown in FIGS. 8A and 8B is illustrated as being covered. A covering can help avoid contaminating the joint with body fluid or debris which could compromise junction function.

Some of the junctions are inherently protected. Junction 176 shown in FIG. 9B comprises a polymer plug 220 or a section of polymer having a different flexibility or durometer than adjacent sections. When a separate piece of polymer is to be employed, it can be chemically, adhesively, or heat welded to adjacent structure; when the junction is formed integrally, this may be accomplished by selective vulcanizing, or reinforcement (even with a braid or by other means of forming a composite structure). Generally, it is noted that any connection of pieces or construction provided may be produced by methods known by those with skill in the art.

Figure 9C:
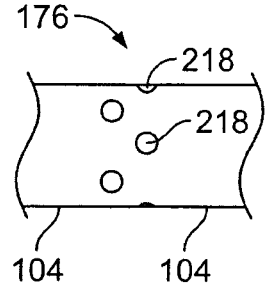
Figure 9D:
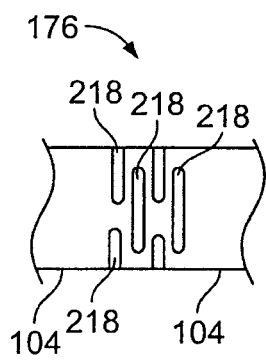

As for junction 176 shown in FIG. 9C, it is formed by removing sections of material from the body of the device. Openings 218 formed at the junction may be left empty, covered or filled with a more compliant material. FIG. 9D also shows a junction 176 in which openings are provided to provide increased flexibility. Here, openings 218 are offset from each other to form a sort of flexible universal joint. In either junction variation shown in FIG. 9C or 9D, the size, number shape, etc. of the opening may vary or be tuned as desired.

Figure 9E:
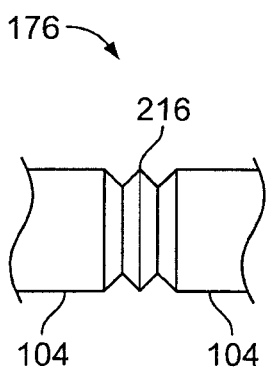

FIG. 9E shows a junction 176 in the form of a bellows comprising plurality of pleats 216. Here too, the number of pleats, etc. may be varied to achieve desirable performance.

Figure 9F:
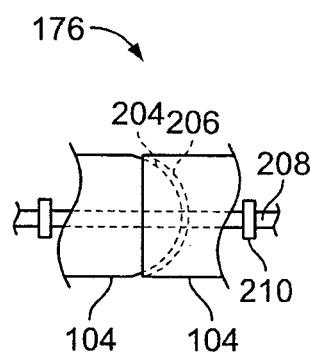

Junction 176 in FIG. 9F shows a true "joint" configuration. In this case, it is a universal joint provided by ball 204 and socket 206. These elements may be held together by a tie wire 208, possibly with caps 210. Other configurations are possible as well.

Figure 9G:
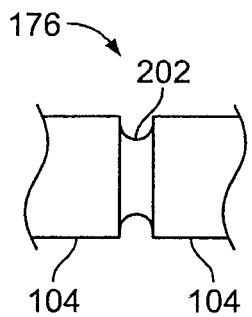
Figure 9H:
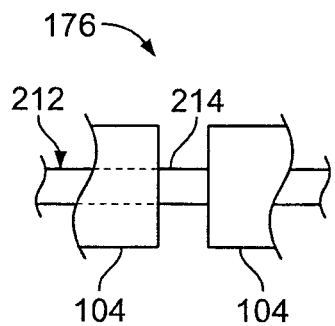

FIG. 9G illustrates a junction 176 in the form of a reduced diameter section 202. This variation offers greater flexibility by virtue of its decreased moment of inertia at the junction. While section 202 is integrally formed, the related junction 176 in FIG. 9H is formed from a hypotube or wire 212 having an exposed junction section 214 on the shaft 104. Variations of the invention will permit a junction having a reduced bending moment of inertia section as compared to the remainder of the device and/or shaft of the device. Reducing the bending moment of inertia may be accomplished in any number of ways. For example, there could be an area of reduced diameter, a section of material having a lower modulus, a section having a different shape, a flexible joint structure, etc. It should be noted that there are many additional ways to reduce the bending moment that will be readily apparent to those skilled in the art viewing the invention disclosed herein.

Figure 9I:
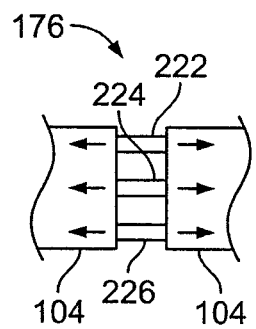

Yet another junction example is provided in FIG. 9I. Here junction 176 comprises a plurality of wires 222, 224, 226. In one variation, the wires simply offer increased flexibility of the junction. In another variation, the wires serve as an "active" or "dynamic" junction. The wires may be adjusted relative to one another to physically steer the distal end of the device. This junction may be manipulated manually with an appropriate user interface—especially one, like a joystick, that allows for full 3-dimensional or rotational freedom—or it may be controlled by automation using appropriate hardware and software controls. Of course, other "dynamic" junctions are possible as well.

Figure 9J:
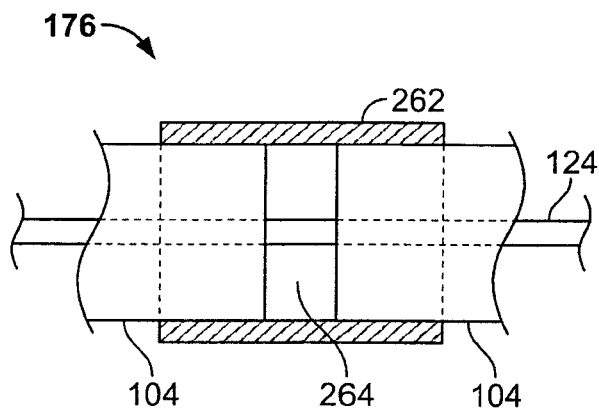

FIG. 9J shows another joint configuration 176 employing an external sleeve 262 between sections of the shaft 104. A moveable wire 124 to actuate a distal basket or the like is also shown. The space between the wire and sleeve may be left open as shown, or filled in with a flexible polymer 264, such as low durometer urethane, a visco-elastic material, etc. Though not necessary, providing an internal member may improve system pushability. The sleeve itself will typically be a polymeric sleeve. It may be heat-shrink material such as PET tubing; it may be integrally formed with either catheter body portion and press fit or slip fit and glued over other etc.

Figure 10A:
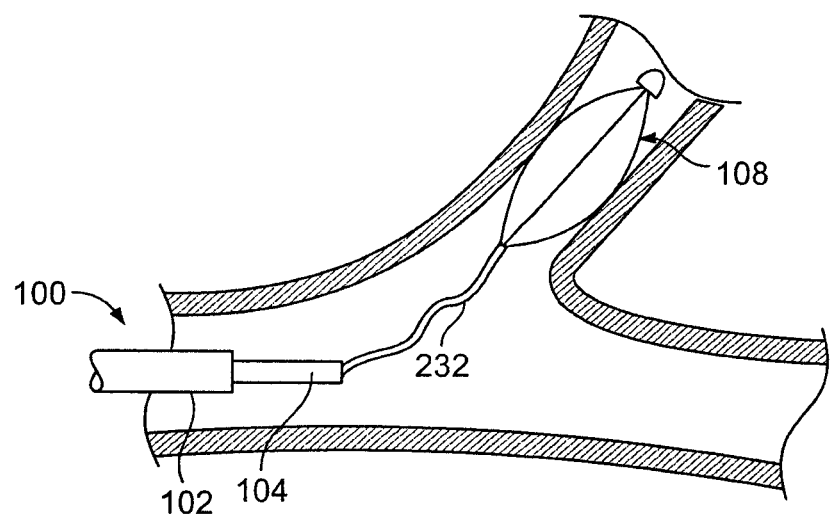
FIGS. 10A-10D shows additional variations of junctions for use in the present devices.

Another variation of the junctions includes junctions variations where the shaft 104 is "floppy" (i.e., without sufficient column strength for the device to be pushable for navigation). In FIG. 10A, a tether 232 connects energy transfer element 108 to the shaft 104 of the device 100. The tether may simply comprise a flexible wire or cable, it may comprise a plurality of links, etc. The tether variation of the invention also accommodates relative motion between the device and the body (e.g., tidal motion of breathing, other muscle contractions, etc.) The tether permits the device to move relative to its intended treatment location unless the user desires and uses the tether or the sheath to pull the device back or drive it forward. The tether may have an alignment component (not illustrated) at the near end of the energy transfer element 108.

To navigate such a device to a treatment site, the energy transfer element 108 and tether 232 may be next to or within the sheath 102. In this manner, the column strength provided by the sheath allows for advancement of the active member within the subject anatomy.

Figure 10B:
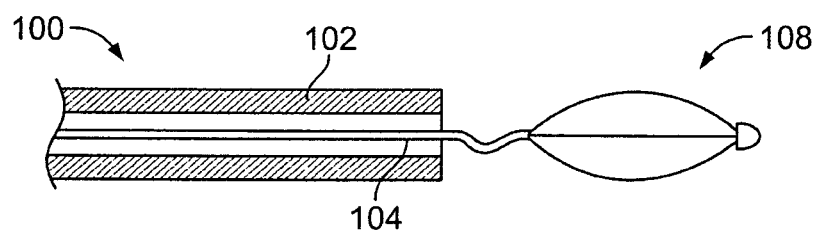

The same action is required to navigate the device shown in FIG. 10B. What differs in this variation of the invention, however, is that the "tether" is actually a continuation of a highly flexible shaft 104. In this case, the shaft 104 of the device is shown with a thicker or reinforced wall. In such a device, the shaft carries the compressive loads on the device back to its distal end.

Figure 10C:
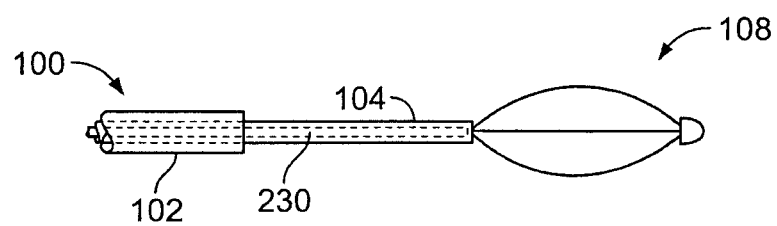
Figure 10D:
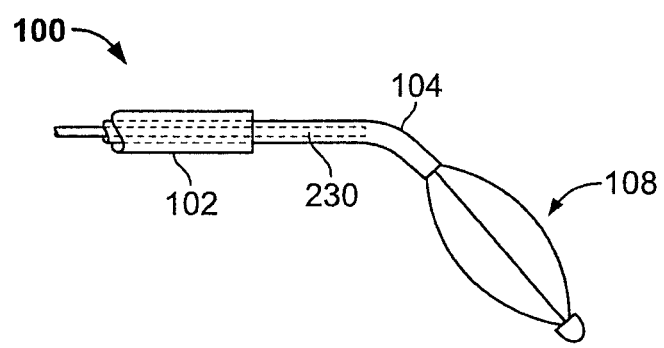

Like the device in FIG. 10B, the devices in FIGS. 10C and 10D have highly flexible shafts 104. However, instead of a stiffening external sheath, the device may employ a stiffening obturator 230 within a lumen of the shaft 104. As shown in FIG. 10C, when the obturator 230 fills the lumen, the device is relatively straight or stiff. When the shaft is withdrawn as shown in FIG. 10D, the distal end of the device is "floppy" or easily conformable to the subject anatomy. With the shaft advanced substantially to the end of the device, it offers ease of navigation; when withdrawn, it offers a compliant section according to an aspect of the present invention.

The inventive device is an energy transfer apparatus which facilitates energy transfer with a mass of tissue within the airways of a lung. The inventive device is sized to enter the bronchus or bronchiole of a human lung to conduct energy transfer with the airway tissue therein. The inventive device may also be sized to fit within a bronchoscope. The bronchoscope may have a channel with a diameter of preferably 2 mm or less.

The ability of the airway to contract can also be altered by treatment of the smooth muscle in particular patterns. The smooth muscle is arranged around the airways in a generally helical pattern with pitch angles ranging from about −30 to about +30 degrees. Thus, the treatment of the smooth muscle by energy which is selectively delivered in an appropriate pattern interrupts or cuts through the helical pattern at a proper pitch and prevents the airway from constricting. This procedure of patterned application of energy eliminates contraction of the airways without completely eradicating smooth muscle and other airway tissue. A pattern for treatment may be chosen from a variety of patterns including longitudinal or axial stripes, circumferential bands, helical stripes, and the like as well as spot patterns having rectangular, elliptical, circular or other shapes. The size, number, and spacing of the treatment bands, stripes, or spots are chosen to provide a desired clinical effect of reduced airway responsiveness while limiting insult to the airway to a clinically acceptable level.

The patterned treatment of the tissues surrounding the airways with energy provides various advantages. The careful selection of the portion of the airway to be treated allows desired results to be achieved while reducing the total healing load. Patterned treatment can also achieve desired results with decreased morbidity, preservation of epithelium, and preservation of a continuous or near continuous ciliated inner surface of the airway for mucociliary clearance. The pattern of treatment may also be chosen to achieve desired results while limiting total treatment area and/or the number of airways treated, thereby improving speed and ease of treatment.

A further process for increasing the airway diameter is by denervation. A resting tone of smooth muscle is nerve regulated by release of catecholamines. Thus, by damaging or eliminating nerve tissue in the airways the resting tone of the smooth muscle will be reduced, and the airway diameter will be increased.

As for other details of the present invention, materials and manufacturing techniques may be employed as within the level of those with skill in the relevant art. The same may hold true with respect to method-based aspects of the invention in terms of additional acts a commonly or logically employed. In addition, though the invention has been described in reference to several examples, optionally incorporating various features, the invention is not to be limited to that which is described or indicated as contemplated with respect to each variation of the invention.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or of the embodiments themselves, where possible. Reference to a singular item, includes the possibility that there are plural of the same items present. More specifically, as used herein and in the appended claims, the singular forms "a," "and," "said," and "the" include plural referents unless the context clearly dictates otherwise.

We claim:

1. A medical device, comprising:
    a catheter extending from a proximal end toward a distal end, the catheter including an inflow lumen and an outflow lumen separate from the inflow lumen;
    a balloon at the distal end of the catheter, the balloon being movable between a collapsed configuration and an expanded configuration; and
    one or more electrodes disposed on an outer surface of the balloon, the one or more electrodes being configured to contact tissues defining a body lumen when the balloon is in the expanded configuration, the one or more electrodes being configured to deliver radiofrequency energy to the tissues defining the body lumen, wherein the inflow lumen is configured to deliver a fluid to the balloon, and the outflow lumen is configured to simultaneously convey the fluid from the balloon, wherein:
    along a given circumferential path that extends around an entirety of the balloon, each of the one or more electrodes has a circumferential length extending circumferentially along the circumferential path; and
    the sum of all of the circumferential lengths of the one or more electrodes covers only a minority of the circumference of the balloon when the balloon is in a maximally-expanded configuration.

2. The medical device of claim 1, wherein delivering the fluid into the balloon inflates the balloon.

3. The medical device of claim 1, wherein the catheter further includes an activation lumen separate from both the inflow lumen and the outflow lumen, and the medical device further includes an energizing member extending from an RF source through the activation lumen to the one or more electrodes.

4. A medical device, comprising:
    a catheter extending from a proximal end toward a distal end, the catheter including an inflow lumen and an outflow lumen separate from the inflow lumen;
    an expandable member at the distal end of the catheter, the expandable member being movable between a collapsed configuration and an expanded configuration; and
    one or more energy delivery elements disposed on an outer surface of the expandable member, the one or more energy delivery elements being configured to contact tissues defining a body lumen when the expandable member is in the expanded configuration, wherein the inflow lumen is configured to deliver a fluid to the expandable member, and the outflow lumen is configured to simultaneously convey the fluid from the expandable member, wherein:
    along a given circumferential path that extends around an entirety of the expandable member, each of the one or more energy delivery elements has a circumferential length extending circumferentially along the circumferential path; and
    the sum of all of the circumferential lengths of the one or more energy delivery elements covers only a minority of the circumference of the expandable member when the expandable member is in a maximally-expanded configuration.

5. The medical device of claim 4, wherein delivering the fluid into the expandable member inflates the expandable member.

6. The medical device of claim 4, wherein the catheter further includes an activation lumen separate from both the inflow lumen and the outflow lumen, and the medical device further includes an energizing member extending from an RF source through the activation lumen to the one or more energy delivery elements.

* * * * *